US011610683B2

(12) United States Patent
Neumann

(10) Patent No.: US 11,610,683 B2
(45) Date of Patent: Mar. 21, 2023

(54) METHODS AND SYSTEMS FOR GENERATING A VIBRANT COMPATIBILITY PLAN USING ARTIFICIAL INTELLIGENCE

(71) Applicant: Kenneth Neumann, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 895 days.

(21) Appl. No.: 16/531,318

(22) Filed: Aug. 5, 2019

(65) Prior Publication Data

US 2021/0042637 A1    Feb. 11, 2021

(51) Int. Cl.
| | | |
|---|---|---|
| *G06Q 30/00* | (2012.01) | |
| *G16H 50/30* | (2018.01) | |
| *G06N 5/04* | (2006.01) | |
| *G16H 20/60* | (2018.01) | |
| *G06F 16/2457* | (2019.01) | |
| *G06N 20/00* | (2019.01) | |

(52) U.S. Cl.
CPC ....... *G16H 50/30* (2018.01); *G06F 16/24578* (2019.01); *G06N 5/04* (2013.01); *G16H 20/60* (2018.01); *G06N 20/00* (2019.01)

(58) Field of Classification Search
None
See application file for complete search history.

(56) References Cited

U.S. PATENT DOCUMENTS 8,560,334 B2 * 10/2013 Lahteenmaki ......... G16H 40/67
                                                    705/2
10,127,361 B2 * 11/2018 Hyde .................... G16H 10/60
(Continued)

OTHER PUBLICATIONS

Maldarelli, Calire; Popular Science, Oct. 25, 2016; A personalized nutrition company will use your DNA to tell you what to eat; https://www.popsci.com/personalized-nutrition-compariy-will-use-your-dna-to-tell-you-what-to-eat.
(Continued)

*Primary Examiner* — Matthew T Sittner
(74) *Attorney, Agent, or Firm* — Caldwell Intellectual Property Law

(57) ABSTRACT

A system for generating a vibrant compatibility plan using artificial intelligence. The system includes at least a server wherein the at least a server is designed and configured to receive at least a composition datum from a user client device wherein the at least a composition datum includes at least an element of user body data and at least an element of desired dietary state data. At least a server is configured to select at least a correlated dataset. At least a server is configured to create at least an unsupervised machine-learning model including at least a hierarchical clustering model to output at least a compatible food element. At least a server is configured to generate at least a vibrant compatibility plan wherein the at least a vibrant compatibility plan further comprises a plurality of compatible food elements each containing at least a food element compatibility index value score as a function of the at least a hierarchical clustering model.

16 Claims, 14 Drawing Sheets

(56) References Cited

U.S. PATENT DOCUMENTS

| | | | |
|---|---|---|---|
| 2005/0080650 A1* | 4/2005 | Noel | G16H 20/60 705/2 |
| 2007/0094090 A1* | 4/2007 | Jenkins | G06Q 30/0643 705/26.5 |
| 2013/0304488 A1* | 11/2013 | Girao | G16H 40/20 705/2 |
| 2015/0363860 A1* | 12/2015 | Lantrip | G06Q 30/0631 705/26.7 |
| 2015/0371553 A1* | 12/2015 | Vento | G09B 19/0092 434/127 |
| 2016/0307128 A1* | 10/2016 | Herman | G06Q 20/202 |
| 2018/0182479 A1* | 6/2018 | Castellon | G16H 50/30 |
| 2018/0189636 A1* | 7/2018 | Chapela | A61B 5/681 |
| 2018/0204274 A1* | 7/2018 | Shimokawa | G06Q 30/0643 |
| 2018/0240542 A1* | 8/2018 | Grimmer | G16H 20/60 |
| 2019/0290172 A1* | 9/2019 | Hadad | G06N 20/00 |

OTHER PUBLICATIONS

Polito, Lisa; Dec. 2, 2016; 3 companies expand the possibuities of personalized nutrition; htips://www.newhope.com/products-and-trends/3-companies-expand-possibilities-personalized-nutrition.

Jones, Alexandra; Sep. 22, 2018; The Guardian; Blood, spit and swabs: can you trust home medical-testing kits?; https://www.theguardian.com/global/2018/sep/22/home-medical-testing-kits-blood-spit-swabs-trust-diy.

Habit Food Personalized; 2019; https://habit.com/how-it-works/.

Van Ommen, et al.; Nutrition Reviews vol. 75; Systems biology of personalized nutrition; https://watermark.silverchair.com/nux029.pdf?

* cited by examiner

| Jerusalem Artichoke Table 700 | |
|---|---|
| Column 1 | Column 2 |
| Nutritional Biomarker 1 | Compatibility Index Value 1 |
| Nutritional Biomarker 2 | Compatibility Index Value 1 |
| Nutritional Biomarker 3 | Compatibility Index Value 2 |
| Nutritional Biomarker X | Compatibility Index Value 3 |
| Body Datum 1 | Compatibility Index Value 4 |
| Body Datum 2 | Compatibility Index Value 5 |
| Body Datum 3 | Compatibility Index Value 6 |
| Body Datum X | Compatibility Index Value 7 |
| Dietary State 1 | Compatibility Index Value 8 |
| Dietary State 2 | Compatibility Index Value 9 |
| Dietary Staate 3 | Compatibility Index Value 10 |
| Dietary State X | Compatibility Index Value 11 |
| Food Element 1 | Compatibility Index Value 12 |
| Food Element 2 | Compatibility Index Value 13 |
| Food Element 3 | Compatibility Index Value 14 |
| Food Element X | Compatibility Index Value 15 |

FIG. 8

METHODS AND SYSTEMS FOR GENERATING A VIBRANT COMPATIBILITY PLAN USING ARTIFICIAL INTELLIGENCE

FIELD OF THE INVENTION

The present invention generally relates to the field of artificial intelligence. In particular, the present invention is directed to methods and systems for generating a vibrant compatibility plan using artificial intelligence.

BACKGROUND

Accurate analysis of datasets can be challenging due to the vast amount of data to be analyzed. Incorrect analysis can lead to inaccuracies and frustrate users. Ensuring accurate selection and implementation is important.

SUMMARY OF THE DISCLOSURE

In an aspect, a system for generating a vibrant compatibility plan using artificial intelligence. The system includes at least a server. The at least a server is designed and configured to receive at least a composition datum from a user client device, generated as a function of at least a user conclusive label and at least a user dietary response, wherein the at least a composition datum further comprises at least an element of user body data and at least an element of desired dietary state data and the at least a user conclusive label contains at least an incompatible food element generated as a function of at least a conclusive label neutralizer. The at least a server is designed and configured to select at least a correlated dataset containing a plurality of data entries wherein each dataset contains at least a datum of body data and at least a correlated compatible food element as a function of the at least a composition datum. The at least a server is designed and configured to create at least an unsupervised machine-learning model wherein the at least an unsupervised machine-learning model further comprises generating a hierarchical clustering model to output at least a compatible food element as a function of the at least a composition datum and the at least a correlated dataset. The at least a server is designed and configured to generate at least a vibrant compatibility plan wherein the at least a vibrant compatibility plan further comprises a plurality of compatible food elements each containing at least a food element compatibility index value score as a function of the at least a hierarchical clustering model.

In an aspect, a method of generating a vibrant compatibility plan using artificial intelligence. The method includes receiving by at least a server at least a composition datum from a user client device, generated as a function of at least a user conclusive label and at least a user dietary response, wherein the at least a composition datum further comprises at least an element of user body data and at least an element of desired dietary state data and the at least a user conclusive label contains at least an incompatible food element generated as a function of at least a conclusive label neutralizer. The method includes selecting by the at least a server at least a correlated dataset containing a plurality of data entries wherein each dataset contains at least datum of body data and at least a correlated compatible food element as a function of the at least a composition datum. The method includes creating by the at least a server at least an unsupervised machine-learning model wherein the at least an unsupervised machine-learning algorithm further comprises generating a hierarchical clustering model to output at least a compatible food element as a function of the at least a composition datum and the at least a correlated dataset. The method includes generating by the at least a server at least a vibrant compatibility plan wherein the at least a vibrant compatibility plan further comprises a plurality of compatible food elements each containing a least a food element compatibility index value score as a function of the at least a hierarchical clustering model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 8 is a block diagram illustrating an exemplary embodiment of a table contained within food element compatibility index value database;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a vibrant compatibility plan using artificial intelligence. In an embodiment, at least a server receives at least a composition datum from a user client device wherein the at least a composition datum includes at least an element of user body data and at least an element of desired dietary state data. In an embodiment, at least an element of user body data may include a nutritional biomarker such as a blood testing indicating the absence or presence of a particular gene. At least a server selects at least a correlated dataset containing a plurality of data entries wherein each dataset contains at least a datum of body data and at least a correlated compatible food element as a function of the at least a composition datum. For example, at least a server may select at least a dataset that contains body data that may match body data contained within at least a composition datum such as the same nutritional biomarker. At least a server creates at least an unsupervised machine-learning model wherein the at least an unsupervised machine-learning model further comprises generating a hierarchical clustering model to output at least a compatible food element as a function of the at least a composition datum and the at least a correlated dataset. At least a server generates at least a vibrant compatibility plan wherein the at least a vibrant compatibility plan further comprises a plurality of compatible food elements each containing at least a food element compatibility index value score as a function of the at least a hierarchical clustering.

Figure 1:
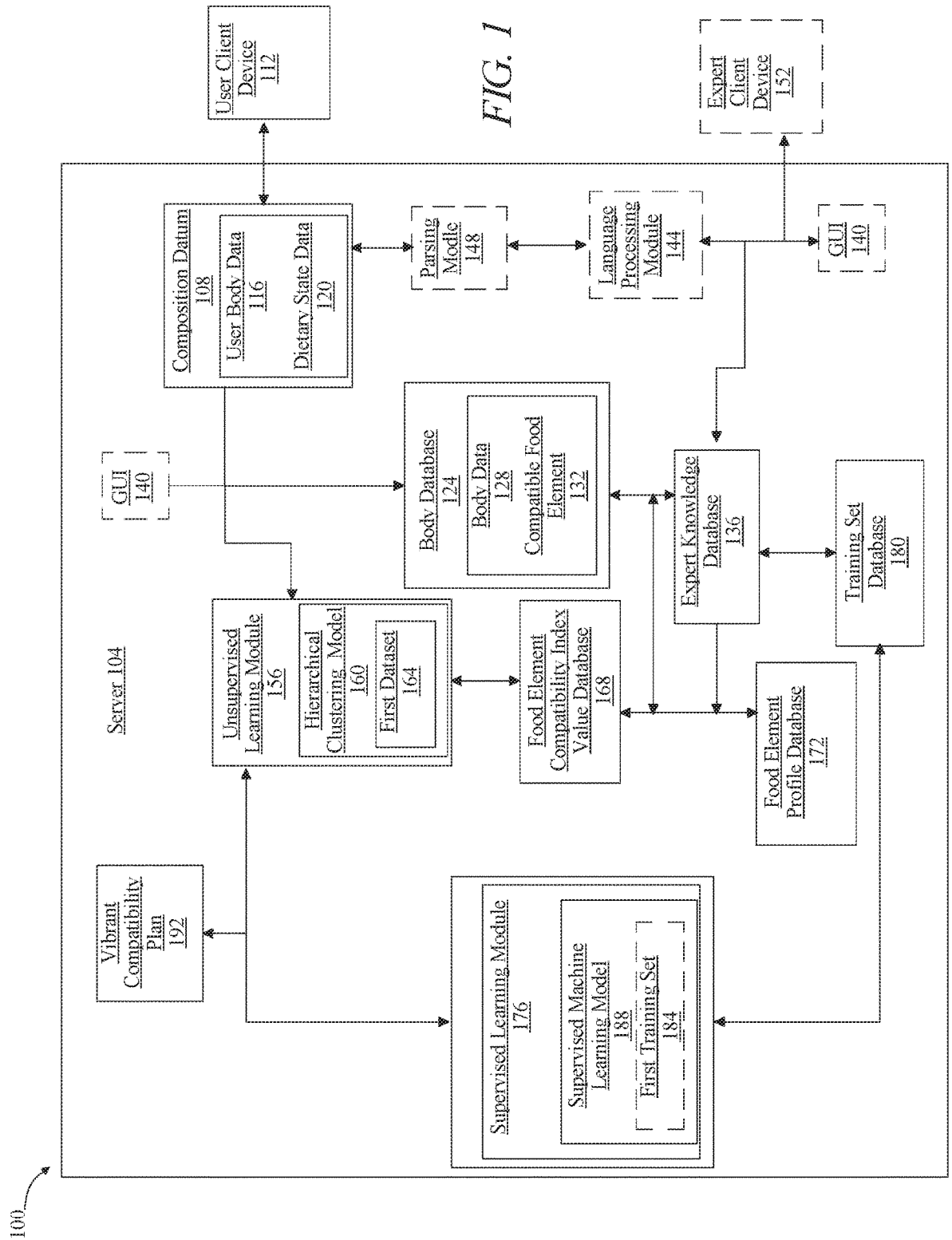
FIG. 1 is a block diagram illustrating an exemplary embodiment of a system for generating a vibrant compatibility plan using artificial intelligence.

Turning now to FIG. 1, a system 100 for generating a vibrant compatibility plan using artificial intelligence is illustrated. System 100 includes at least a server 104. At least a server 104 may include any computing device as described herein, including without limitation a microcontroller, microprocessor, digital signal processor (DSP) and/or system on a chip (SoC) as described herein. At least a server 104 may be housed with, may be incorporated in, or may incorporate one or more sensors of at least a sensor. Computing device may include, be included in, and/or communicate with a mobile device such as a mobile telephone or smartphone. At least a server 104 may include a single computing device operating independently, or may include two or more computing device operating in concert, in parallel, sequentially or the like; two or more computing devices may be included together in a single computing device or in two or more computing devices. At least a server 104 with one or more additional devices as described below in further detail via a network interface device. Network interface device may be utilized for connecting a at least a server 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 104 may include but is not limited to, for example, a at least a server 104 or cluster of computing devices in a first location and a second computing device or cluster of computing devices in a second location. At least a server 104 may include one or more computing devices dedicated to data storage, security, distribution of traffic for load balancing, and the like. At least a server 104 may distribute one or more computing tasks as described below across a plurality of computing devices of computing device, which may operate in parallel, in series, redundantly, or in any other manner used for distribution of tasks or memory between computing devices. At least a server 104 may be implemented using a "shared nothing" architecture in which data is cached at the worker, in an embodiment, this may enable scalability of system 100 and/or computing device.

With continued reference to FIG. 1, at least a server 104 is configured to receive at least a composition datum 108 from a user client device 112 generated as a function of at least a user conclusive label and at least a user dietary response, wherein the at least a composition datum further comprises at least an element of user body data and at least an element of desired dietary state data. Composition datum 108, as used herein, includes any data describing and/or relating to a nutritional state of a user. Nutritional state, as used herein includes the dietary requirements of a user and any associated nutrient levels, nutrient biomarkers, and/or biological samples obtained from a physically extracted sample of a user. Physically extracted sample, as used herein, includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a physically extracted sample may include an epigenetic sample, a proteomic sample, a tissue sample, a biopsy, and/or any other physically extracted sample. At least a biological extraction may include an endocrinal sample. As a further non-limiting example, the at least a biological extraction may include a signal from at least a sensor configured to detect physiological data of a user and recording the at least a biological extraction as a function of the signal. At least a sensor may include any sensor and/or device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, and/or blood pressure.

At least a sensor may be a part of at least a server 104 or may be a part of a separate device in communication with at least a server 104.

With continued reference to FIG. 1, nutritional state may include any data indicative of a person's nutritional biomarkers; nutritional state may be evaluated with regard to one or more measures of health of a person's body, one or more systems within a person's body such as a digestive system, a circulatory system, or the like, one or more organs within a person's body, one or more body dimensions of a person's body; and/or any other subdivision of a person's body useful for nutritional evaluation. Nutritional biomarkers may include, without limitation, one or more intracellular or extracellular measurements of vitamin levels such as Vitamin A, Vitamin B2, Vitamin D and the like. Nutritional biomarkers may include, without limitation, one or more intracellular or extracellular measurements of mineral levels such as calcium, magnesium, and iron. Nutritional biomarkers may include, without limitation, one or more intracellular or extracellular measurements of metabolites such as choline, inositol, and carnitine. Nutritional biomarkers may include; without limitation, one or more intracellular or extracellular measurements of electrolytes such as sodium and potassium. Nutritional biomarkers may include, without limitation, one or more intracellular or extracellular measurements of amino acids such as asparagine, glutamine, and serine. Nutritional biomarkers may include, without limitation, one or more intracellular or extracellular measurements of antioxidants such as Coenzyme Q10, cysteine, and glutathione. Nutritional biomarkers may include, without limitation, one or more intracellular or extracellular measurements of fatty acids and omega acids such as eicosatetraenoic acid (EPA), docosahexaenoic acid (DHA), and total omega 3 levels. Nutritional biomarkers may include, without limitation, one or more microbiome measurements such as stool tests that identify microorganisms living within a gut such as strains and/or quantities of bacteria, archaea, fungi, protozoa, algae, viruses; parasites, words, and the like. Nutritional biomarker may include, without limitation, one or more genetic measurements such as APOE gene that is involved in transportation of blood lipids such as cholesterol or MTHFR gene that is involved in making enzymes involved in metabolism and utilization of Vitamin B9 or FTO gene that is involved in a user's ability to feel full or satiated. Nutritional biomarker may include, without limitation, one or more gut wall measurements such as data describing on gut wall function, gut wall integrity, gut wall strength, gut wall absorption, gut wall permeability, intestinal absorption, gut wall absorption of bacteria. Gut wall measurements may include for example blood levels of creatinine levels or breath levels of lactulose, hydrogen, methane, lactose and the like. Nutritional biomarker may include one or more measurement of cognitive function, including any data generated using psychological, neuro-psychological and/or cognitive evaluations as well as diagnostic screening tests; personality tests, personal compatibly tests or the like.

With continued reference to FIG. 1, composition datum 108 includes at least an element of user body data 116 and at least an element of desired dietary state data. User body data 116, as used herein, includes any nutritional biomarker, including any of the nutritional biomarkers as described above. For instance and without limitation, nutritional biomarker may include a salivary hormone panel that contains levels of estradiol, estrone, estriol, progesterone, testosterone, cortisol, and melatonin. In yet another non-limiting example, nutritional biomarker may include a blood sample result showing plasma levels of amino acids and metabolites utilized in folate metabolism and synthesis in the body. In yet another non-limiting example, nutritional biomarker may include a user self-reported previous diagnosis, medical condition, dietary elimination, self-diagnosis, dietary lifestyle, nutritional belief, nutritional habit and the like. For instance and without limitation, nutritional biomarker may include a user's self-reported gluten intolerance or a user's aversion to consume animal products. Nutritional biomarker may include a user's inability to consume a particular food or food group for religious reasons or an inability to consume a particular food or food group due to an immunoglobulin E (IGE) mediated response or an immunoglobulin G (IGG) mediated response. In yet another non-limiting example, nutritional biomarker may include a user's preference to consume certain foods or a user's self-described dietary elimination diet.

With continued reference to FIG. 1, composition datum 108 includes at least an element of desired dietary state data. Desired dietary state data, as used herein, includes a user's goal eating habits and/or current eating habits. Eating habits as used herein, includes any data describing a user's food preferences, food allergies, food intolerances, style of eating, diet that a user may be following; meal types, and the like. Desired dietary state data 120 may include for example a user's goal to consume a gluten free diet or a diet free of artificial colors. Desired dietary state may be received as a function of a user conclusive label.

With continued reference to FIG. 1, at least a composition datum is generated as a function of at least a user conclusive label and at least a user dietary response. User conclusive label as used herein, includes an element of data identifying and/or describing a current, incipient, or probable future medical condition affecting a person; medical condition may include a particular disease, one or more symptoms associated with a syndrome, a syndrome, and/or any other measure of current or future health and/or healthy aging. For example, user conclusive label may include an element of data indicating a diagnosis of a user from a medical professional such as for example, a diagnosis of celiac disease by a medical professional or a diagnosis of Vitamin C deficiency from a nutritionist. User conclusive label may be associated with a physical and/or somatic condition, a mental condition, a chronic infection, an immune disorder, a metabolic disorder, a connective tissue disorder, an excretory system disorder, a liver disorder, a joint disorder, a cancer, and the like. User conclusive label may be associated with a descriptor of latent, dormant, and/or apparent disorders, diseases, and/or conditions. User conclusive labels may include descriptors of conditions for which a person may have a higher than average probability of development such as a condition for which a person may have a "risk factor" such as for example a person suffering from abdominal obesity may have a higher than average probability of developing type II diabetes. In an embodiment, desired dietary state may be received as a function of a user conclusive label, such as for example when a medical professional may prescribe or desire a particular nutritional state linked to a user conclusive label. For instance and without limitation, a medical professional may prescribe a particular dietary state such as a vegan diet for a user with heart disease or a low carbohydrate diet for a user with a systemic *Candida albicans* infection. In yet another non-limiting example, a medical professional may prescribe a particular dietary state such as a diet rich in carbohydrates that contain B Vitamins for a user with alcoholism or a diet free of added sugars for a user with diabetes mellitus type 2.

With continued reference to FIG. 1, at least an element of desired dietary state data may be received as a function of a user generated dietary response. User generated dietary response may include a user's own preference for a particular desired dietary state. For instance and without limitation, user may experience gas, bloating, diarrhea, and nausea after eating dairy containing foods such as milk, cheese, and ice cream. In such an instance, user may choose to eliminate such foods and generate a desired dietary state datum that includes a preference to consume a dairy free diet. In yet another non-limiting example, user may read in a magazine about a paleo diet being able to help individuals lose weight, whereby user may choose to follow a paleo diet. In such an instance, user may generate a desired dietary state datum that includes a preference to consume a paleo diet. In an embodiment, element of user body data 116 and element of desired dietary state data 120 may contain the same input. For example, element of user body data 116 may include a nutritional biomarker that contains a user self-reported elimination of food products containing nightshades and element of desired dietary state data 120 may contain an input containing a desire to follow a nightshade free diet. In an embodiment, user generated dietary response may be generated from a survey or questions that a user may answer. For example, user may respond to a series of prompted questions asking user about user's eating habits, user's eating preferences, foods that user routinely consumes and the like.

With continued reference to FIG. 1, at least a server 104 receives at least a composition datum from a user client device generated as a function of at least a user conclusive label and at least a user dietary response. In an embodiment, user conclusive label such as a previous diagnosis of Multiple Sclerosis may be used to generate a desired dietary state that includes the Swank diet, and an element of user body data that includes a previously recorded magnetic resonance image (MRI). In an embodiment, user conclusive label may not contain a description, such as when a user has no known medical conditions or may not take any medications or supplements. In yet another non-limiting example, a user may utilize a previous diagnosis from childhood such as an anaphylactic response to tree nuts to generate a composition datum that includes a desired dietary state that does not contain tree nuts and an element of body data that contains symptoms of an anaphylactic reaction that a user experiences upon consumption of tree nuts and tree nut containing products such as rash, itchiness, hives, and throat swelling. In an embodiment, dietary response may be utilized to generate at least a composition datum. For example, a user may prefer to eliminate dairy products due to experiencing symptoms such as gas, bloating, and diarrhea after consuming dairy products. In such an instance, user may generate a composition datum that includes a body datum such as symptoms user experiences upon consuming dairy products and dietary state data that includes a diet free of dairy products. In yet another non-limiting example, a user may for example, perform a direct to consumer health test at home without the supervision of a medical professional that provides a user with results of a stool sample analysis containing an analysis of microbial species that may be present and/or absent within user's gastrointestinal tract. In such an instance, user may generate at least a composition datum containing body datum which includes stool sample analysis and at least a dietary response that may not select any one particular dietary state.

With continued reference to FIG. 1, at least a server 104 is configured to receive at least a user conclusive label containing at least an incompatible food element as a function of at least a conclusive label neutralizer. Incompatible food element, as used herein, includes any food element that a user does not seek to consume. User may not consume a particular food element for religious reasons, ethical concerns, dislike of a particular food, an allergy to a particular food whether due to anaphylaxis, an intolerance, symptomology, and the like, and or any other reason that a user may not consume a particular food element. Incompatible food element may be generated as a function of at least a conclusive label neutralizer. Conclusive label neutralizer, as used herein, includes any process that may improve any physical condition identifiable in a conclusive label. Conclusive label neutralizer may include medications, supplements, nutrients, herbal remedies, exercise programs, medical procedures, physical therapies, psychological therapies, and the like. For example, conclusive label neutralizer may include a specific medication designed to treat a user's nail fungus or conclusive label neutralizer may include a particular supplement utilized to balance out a user's symptoms of estrogen dominance. User conclusive label may be generated as a function of a conclusive label neutralizer, such as when a certain medication, supplement, and/or medical procedure may be associated with incompatible food elements. For example, a conclusive label neutralizer such as a statin medication that is utilized to reduce total cholesterol levels may be utilized to generate an incompatible food element that includes grapefruit and grapefruit containing food products. In yet another non-limiting example, a conclusive label neutralizer such as doxycycline for acne may be utilized to generate an incompatible food element that includes dairy products. In yet another non-limiting example, a conclusive label neutralizer such as high-intensity training may be utilized to generate an incompatible food element such as grain products as part of a paleo-centered approach often coupled with high-intensity training.

With continued reference to FIG. 1, at least a server 104 is designed and configured to receive at least a user dietary response containing at least an acute vibrancy input, at least a chronic vibrancy input, and at least a longevity vibrancy input. Acute vibrancy input, as used herein, includes any short-term dietary response. For example, acute vibrancy input may include elimination of certain food elements such as cookies, donuts, and cakes because of an upcoming wedding or event such as a graduation. In yet another non-limiting example, acute vibrancy input may include a desire to eliminate all carbohydrates from one's diet for three months before a spring break trip to Medico. Chronic vibrancy input, as used herein, includes any chronic dietary response. For example, chronic vibrancy input may include elimination of certain food elements as part of an ongoing health plan or health goal. For example, a chronic vibrancy input may include a chronic elimination of food elements such as sugar due to an ongoing health plan to lose weight. In yet another non-limiting example, a chronic vibrancy input may include a chronic elimination of nightshades food elements such as tomatoes and eggplant as part of an ongoing elimination diet. Longevity vibrancy input, as used herein, includes any lifelong dietary response. For example, longevity vibrancy input may include a permanent elimination of simple carbohydrates for a user with a chronic medical condition such as diabetes. In yet another non-limiting example, longevity vibrancy input may include elimination of food elements high in saturated fat such as coconut and shrimp for a user with heart disease.

With continued reference to FIG. 1, a user client device 112 may include, without limitation, a display in communication with at least a server 104; display may include any display as described herein. A user client device 112 may include an additional computing device, such as a mobile device, laptop, desktop computer, or the like; as a non-limiting example, the user client device 112 may be a computer and/or workstation operated by a medical professional. Output may be displayed on at least a user client device 112 using an output graphical user interface 140, as described in more detail below. Transmission to a user client device 112 may include any of the transmission methodologies as described herein.

With continued reference to FIG. 1, at least a server 104 is configured to select at least a correlated dataset containing a plurality of data entries wherein each dataset contains at least a datum of body data and at least a correlated compatible food element as a function of the at least a composition datum 108. Body data, as used herein, includes any of the data suitable for use as user body data 116 as described above. For instance and without limitation, body data may include blood results showing particular extracellular levels of nutrients such as Vitamin D, Vitamin K, and Vitamin 1. In yet another non-limiting example, body data may include stool results showing particular biomarkers within a gastrointestinal tract such as for example, beneficial short-chain fatty acids (SCFA) with n-butyrate, fecal lactoferrin, beneficial bacteria, additional bacteria and the like. In yet another non-limiting example, body data may include a particular diet or way of eating such as for example a macrobiotic diet or a low FODMAP diet. Datasets may be selected and contained within body database 124 as described below in more detail in reference to FIG. 2.

With continued reference to FIG. 1, each dataset contains at least a datum of body data 128 and at least a correlated compatible food element 132. Compatible food element as used herein, includes any element of data identifying and/or describing any food substance that a user may consume as a function of a datum of body data. Food substance, as used herein, includes any substance consumed to provide nutritional support for an organism such as a human being. Food substance may include for example, a particular food such as kale, cabbage, and chicken. Food substance may include a category of food that may be categorized as having a shared characteristic or trait. For example, food substance may include categories such as dairy products, vegetables, animal proteins, seafood, fats, carbohydrates, and the like. In an embodiment, at least a datum of body data is correlated with a compatible food element where the element of body data is located in the same data element and/or portion of data element as the body data; for example, and without limitation, an element of body data is correlated with a compatible food element where both element of body data and compatible food element are contained within the same first dataset 164 or are both collected from the same user. For instance and without limitation, body data showing an overgrowth of yeast in a user's gastrointestinal tract may be correlated to a compatible food element such as garlic which is shown to be effective in killing *Candida albicans*. In yet another non-limiting example, body data showing low salivary levels of progesterone may be correlated to a compatible food element such as pumpkin, sweet potato, and broccoli.

With continued reference to FIG. 1, dataset containing plurality of data entries wherein each dataset contains at least a datum of body data and at least a correlated compatible food element may be stored in a body database as described in more detail below in reference to FIG. 2. Dataset may be stored in any suitable data and/or data type. For instance and without limitation, dataset may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as dataset may take; persons skilled in the art, upon reviewing the entirety of this disclosure, will be aware of various forms which may be suitable for use as dataset consistently with this disclosure.

With continued reference to FIG. 1, dataset may be stored as image data, such as for example an image of a particular food substance such as a photograph of a pear or an image of a steak. Image data may be stored in various forms including for example, joint photographic experts group (PEG), exchangeable image file format (Exif), tagged image file format (TIFF), graphics interchange format (GIF), portable network graphics (PNG), netpbm format, portable bitmap (PBM), portable any map (PNM), high efficiency image file format (HEIF), still picture interchange file format (SPIFF), better portable graphics (BPG), drawn filed, enhanced compression wavelet (ECW), flexible image transport system (FITS), free lossless image format (FLIF), graphics environment manage (GEM), portable arbitrary map (PAM), personal computer exchange (PCX), progressive graphics file (PGF), gerber formats, 2 dimensional vector formats, 3 dimensional vector formats, compound formats including both pixel and vector data such as encapsulated postscript (EPS), portable document format (PDF), and stereo formats.

With continued reference to FIG. 1, datasets contained within body database may be obtained from a plurality of sources. Datasets contained within body database may contain a plurality of data entries, obtained for example, from patient medical records that have been stripped of identifying information. Datasets contained within body database may be obtained from patient surveys who may be sampled in a variety of methods such as by phone, mail, internet and the like. Patient surveys may be distributed to patients across a breadth of geographical locations and may also be stripped of identifying information. Datasets contained within body database may be obtained from clinical data such as from facilities including nursing homes, hospitals, home health agencies, and the like as described below in more detail in reference to FIG. 6.

With continued reference to FIG. 1, datasets contained within body database may be obtained from an expert knowledge database. Expert knowledge database 136 may include data entries reflecting one or more expert submissions of data such as may have been submitted according to any process, including without limitation by using graphical user interface 140. Information contained within expert knowledge database 136 may be received from input from expert client device. Expert client device may include any device suitable for use as user client device 112 as described above. Expert knowledge database 136 may include one or more fields generated by a language processing module, such as without limitation fields extracted from one or more documents such as for example medical journals, scientific journals, medical articles, scientific articles, medical reviews, scientific reviews, medical trials, scientific trials and the like. Documents may be stored and/or retrieved by at least a server 104 and/or language processing module 144 in and/or from a document database. Documents in document database may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, data, or the like as consistent with this disclosure.

With continued reference to FIG. 1, at least a server 104 may receive a list of significant categories of body data and/or compatible food elements from at least an expert. In an embodiment, at least a server 104 may provide a graphical user interface 140, which may include without limitation a form or other graphical element having data entry fields, wherein one or more experts, including without limitation clinical and/or scientific experts, may enter information describing one or more categories of body data that the experts consider to be significant or useful for detection of conditions; fields in graphical user interface 140 may provide options describing previously identified categories, which may include a comprehensive or near-comprehensive list of types of user input datums detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface 140 or the like may include fields corresponding to correlated compatible food elements, where experts may enter data describing compatible foods the experts consider related to entered categories of body data; for instance, such fields may include drop-down lists or other pre-populated data entry fields listing currently recorded body data, and which may be comprehensive, permitting each expert to select a compatible food element the expert believes to be predicted and/or associated with each category of body data selected by the expert. Fields for entry of body data and/or compatible food elements may include free-form data entry fields such as text entry fields; as described above, examiners may enter data not presented in pre-populated data fields in the free-form data entry fields. Alternatively or additionally, fields for entry of body data and/or compatible food elements may enable an expert to select and/or enter information describing or linked to a category of body data that the expert considers significant, where significance may indicate likely impact on longevity, mortality, quality of life, or the like as described in further detail below. Graphical user interface 140 may provide an expert with a field in which to indicate a reference to a document describing significant categories of body data, relationships of such categories to compatible food elements, and/or significant categories of compatible food elements. Any data described above may alternatively or additionally be received from experts similarly organized in paper form, which may be captured and entered into data in a similar way, or in a textual form such as a portable document file (PDF) with examiner entries, or the like.

With continued reference to FIG. 1, data information describing significant categories of body data, relationships of such categories to compatible food element may be extracted from one or more documents using a language processing module 144. Language processing module 144 may include any hardware and/or software module. Language processing module 144 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 144 may compare extracted words to categories of body data recorded by at least a server 104, and/or one or more categories of compatible food substances recorded by at least a server 104; such data for comparison may be entered on at least a server 104 as using expert data inputs or the like. In an embodiment; one or more categories may be enumerated, to find total count of mentions in such documents. Alternatively or additionally, language processing module 144 may operate to produce a language processing model. Language processing model may include a program automatically generated by at least a server 104 and/or language processing module 144 to produce associations between one or more words extracted from at least a document and detect associations, including without limitation mathematical associations, between such words, and/or associations of extracted words with categories of user input datums, relationships of such categories to first probing elements, and/or categories of first probing elements. Associations between language elements; where language elements include for purposes herein extracted words, categories of user input datums, relationships of such categories to first probing elements, and/or categories of first probing elements may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of user input datum, a given relationship of such categories to a first probing element, and/or a given category of a first probing element. As a further example, statistical correlations and/or mathematical associations may include probabilistic formulas or relationships indicating a positive and/or negative association between at least an extracted word and/or a given category of body data, a given relationship of such categories to compatible food element, and/or a given category of compatible food element; positive or negative indication may include an indication that a given document is or is not indicating a category of body data, relationship of such category to a first compatible food element, and/or category of compatible food elements is or is not significant. For instance, and without limitation, a negative indication may be determined from a phrase such as "High stool fungal overgrowth was not found to be compatible with high fructose corn syrup" whereas a positive indication may be determined from a phrase such as "Low serum sodium levels was found to be compatible with sea salt" as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory by at least a server 104, or the like.

Still referring to FIG. 1, language processing module 144 and/or at least a server 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein, are statistical models with inference algorithms that that may be applied to the models. In such models, a hidden state to be estimated may include an association between an extracted word category of body data, a given relationship of such categories to compatible food element, and/or a given category of compatible food elements. There may be a finite number of category of body data a given relationship of such categories to a compatible food element, and/or a given category of food elements to which an extracted word may pertain; an HMM inference algorithm, such as the forward-backward algorithm or the Viterbi algorithm, may be used to estimate the most likely discrete state given a word or sequence of words. Language processing module 144 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 144 may use a corpus of documents to generate associations between language elements in a language processing module 144 and at least a server 104 may then use such associations to analyze words extracted from one or more documents and determine that the one or more documents indicate significance of a category of body data, a given relationship of such categories to compatible food elements, and/or a given category of food elements. In an embodiment, at least a server 104 may perform this analysis using a selected set of significant documents, such as documents identified by one or more experts as representing good science, good clinical analysis, or the like; experts may identify or enter such documents via graphical user interface 140, or may communicate identities of significant documents according to any other suitable method of electronic communication, or by providing such identity to other persons who may enter such identifications into at least a server 104. Documents may be entered into at least a server 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URI) or other datum permitting unambiguous identification of the document, at least a server 104 may automatically obtain the document using such an identifier, for instance by submitting a request to a database or compendium of documents such as JSTOR as provided by Ithaka Harbors; Inc. of New York.

With continued reference to FIG. 1, at least a server may be configured to extract at least a physiological trait from at least a composition datum 108 and match the at least a physiological treat to at least a correlated dataset containing at least an element of the at least a physiological trait. Physiological trait, as used herein, includes information, data, and/or description relating a functioning of a user's body. Physiological trait may include any data suitable for use as body data as described above, including for example any nutritional biomarker. For example, physiological data may include a measured blood value of a nutrient such as zinc, a stool test reflecting a bacterial count, bacterial species, and the like. Physiological trait may include a nutritional biomarker such as a mutation of the congenital lactase deficiency gene or a mutation of TCF7L2 gene that regulates insulin secretion.

With continued reference to FIG. 1 physiological trait may be extracted from a composition datum 108 by a parsing module 148 operating on at least a server 104. Parsing module 148 may parse at least a composition datum 108 for at least a physiological trait and match the at least a physiological trait to at least a correlated dataset containing at least an element of the at least a physiological trait. In an embodiment, datasets contained within body database may be categorized by physiological traits, as described in more detail below in reference to FIG. 2. Parsing module 148 may match at least a dataset by extracting one or more keywords containing words, phrases, test results, numerical scores, and the like from composition datum 108 and analyze the one or more keywords utilizing for example, language processing module 144 as described in more detail below. Parsing module 148 may be configured to normalize one or more words or phrases of user input, where normalization signifies a process whereby one or more words or phrases are modified to match corrected or canonical forms; for instance, misspelled words may be modified to correctly spelled versions, words with alternative spellings may be converted to spellings adhering to a selected standard, such as American or British spellings, capitalizations and apostrophes may be corrected, and the like; this may be performed by reference to one or more "dictionary" data structures listing correct spellings and/or common misspellings and/or alternative spellings, or the like. Parsing module 148 may perform algorithms and calculations when analyzing tissue sample analysis and numerical test results. For instance and without limitation, parsing module 148 may perform algorithms that may compare test results contained within composition datum 108, tissue analysis results, and/or biomarker levels to normal reference ranges or values. For example, parsing module 148 may perform calculations that determine how many standard deviations from normal levels a salvia hormone test containing salivary levels of progesterone are from normal reference ranges. In yet another non-limiting example, parsing module 148 may perform calculations between different values contained within composition datum 108. For example, parsing module 148 may calculate a ratio of progesterone to estradiol levels from a blood test containing a hormone panel that may include progesterone, estradiol, estrone, estriol, and testosterone serum levels.

With continued reference to FIG. 1, parsing module 148 may extract and/or analyze one or more words or phrases by performing dependency parsing processes; a dependency parsing process may be a process whereby parsing module 148 recognizes a sentence or clause and assigns a syntactic structure to the sentence or clause. Dependency parsing may include searching for or detecting syntactic elements such as subjects, objects, predicates or other verb-based syntactic structures, common phrases, nouns, adverbs, adjectives, and the like; such detected syntactic structures may be related to each other using a data structure and/or arrangement of data corresponding, as a non-limiting example, to a sentence diagram, parse tree, or similar representation of syntactic structure. Parsing module 148 may be configured, as part of dependency parsing, to generate a plurality of representations of syntactic structure, such as a plurality of parse trees, and select a correct representation from the plurality; this may be performed, without limitation, by use of syntactic disambiguation parsing algorithms such as, without limitation, Cocke-Kasami-Younger (CKY), Earley algorithm or Chart parsing algorithms. Disambiguation may alternatively or additionally be performed by comparison to representations of syntactic structures of similar phrases as detected using vector similarity, by reference to machine-learning algorithms and/or modules.

With continued reference to FIG. 1, parsing module 148 may combine separately analyzed elements from composition datum 108 to extract and combine at least a keyword. For example, a first test result or biomarker reading may be combined with a second test result or biomarker reading that may be generally analyzed and interpreted together. For instance and without limitation, a nutritional biomarker of zinc may be reading and analyzed in combination with a nutritional biomarker reading of copper as excess zinc levels can deplete copper levels. In such an instance, parsing module 148 may combine nutrition biomarker reading off zinc and biomarker reading of copper and combine both levels to create one keyword. In an embodiment, combinations of tissue sample analysis, keywords, or test results that may be interpreted together may be received from input received from experts and may be stored in an expert knowledge database. Expert client device 152 may include any device suitable for use as user client device 112 as described above.

With continued reference to FIG. 1, at least a server 104 may include an unsupervised machine-learning module 156 operating on at least a server and/or on another computing device in communication with at least a server 104, which may include any hardware or software module. At least a server is configured to create at least an unsupervised machine learning model wherein the at least an unsupervised machine learning model further comprises a hierarchical clustering model 160 to output at least a compatible food element as a function of the at least a composition datum 108 and the at least a correlated dataset. An unsupervised machine-learning process, as used herein, is a process that derives inferences in datasets without regard to labels; as a result, an unsupervised machine-learning process may be free to discover any structure, relationship; and/or correlation provided in the data. For instance, and without limitation, unsupervised machine learning module and/or at least a server 104 may perform an unsupervised machine learning process on a first data set, which may cluster data of first data set according to detected relationships between elements of the first data set, including without limitation correlations of elements of body data to each other and correlations of compatible food element to each other; such relations may then be combined with supervised machine learning results to add new criteria for at supervised machine-learning processes as described in more detail below. As a non-limiting, illustrative example; an unsupervised process may determine that a first body datum correlates closely with a second body datum, where the first element has been linked via supervised learning processes to a given compatible food element, but the second has not; for instance, the second body datum may not have been defined as an input for the supervised learning process; or may pertain to a domain outside of a domain limitation for the supervised learning process. Continuing the example a close correlation between first body datum and second body datum may indicate that the second body datum is also a good predictor for the compatible food element; second body datum may be included in a new supervised process to derive a relationship or may be used as a synonym or proxy for the first body datum.

With continued reference to FIG. 1, hierarchical clustering model 160 may include any method of cluster analysis which outputs a hierarchy of clusters. Cluster analysis, as used herein, includes any grouping of objects such as datasets in such a way that datasets in the same group or cluster are more similar to each other than to those in other clusters. Cluster analysis may include hard clustering and/or soft clustering. Hard clustering may include clustering where each dataset belongs to any particular cluster or not. Soft clustering may include clustering where each dataset may belong to a cluster to a certain degree such as a certain percentage of belonging to any given cluster or a likelihood of belonging to a given cluster. Hierarchical clustering may group and/or segment datasets with shared attributes to extrapolate algorithmic relationships. Hierarchical clustering model 160 may include generating various algorithms that may work to find clusters that may be generated based on parameter settings such as distance functions to use, density threshold, and optimal of clusters to generate. Hierarchical clustering model 160 may include models such as but not limited to connectivity models, centroid models, distribution models, density models, subspace models, group models, graph-based models, signed graph models, neural models, and the like.

With continued reference to FIG. 1, hierarchical clustering model 160 may include agglomerative and/or divisive hierarchical clustering. Agglomerative hierarchical clustering may include a bottom-up approach whereby each observation may start in its own cluster, and pairs of clusters may be merged as one moves up the hierarchy. Divisive hierarchical clustering may include a top-down approach whereby all observations may start in one cluster and splits may be performed recursively moving down the hierarchy.

With continued reference to FIG. 1, at least a server 104 may be configured to retrieve at least a food element compatibility index value correlated to at least a food element from a database and rank the at least a food element as a function of the food compatibility index. Food element compatibility index value, as used herein, is a value assigned to a food element indicating a degree of compatibility between a food element any given element of food data. Food compatibility index value may be stored in a food compatibility index value database operating on at least a server 104. A given food element may contain a plurality of index values each correlated to an element of body data. For example, a food element may contain a first index value correlated to a first element of body data and the same food element may contain a second index value correlated to a second element of body data. Food element compatibility index value may be based on a numerical score whereby a high numerical value may indicate a high degree of compatibility whereby a low numerical value may indicate a low degree of compatibility. Food element compatibility index values may vary for any single variant of any particular body data. For instance and without limitation, a food element such as brie cheese may be correlated to a low food compatibility index value for a first element of body data that shows a G/G genotype of the MCM6 gene that controls production of lactase enzyme and thereby indicates an inability to produce lactase efficiently with the G/G genotype, whereby brie cheese may be correlated to a higher food element compatibility index value for a second element of body data that shows an A/A genotype of the MCM6 gene that indicates an ability to produce lactase efficiently. In an embodiment, food element compatibility index value may include a score relating compatibility between a first food element and a second food element for any given body datum. For example, food element compatibility index value may include a value that reflects the ability for a user with a body datum such as a G/G genotype of the FUT2 gene that controls enzyme production to absorb Vitamin B12 in the digestive tract, to consume a second compatible food element such as lamb based on a high compatibility score for a first food element such as pork. In such an instance, food element compatibility index value may reflect ability to substitute a first compatible food element for a second compatible food element and/or ability to consume a second compatible food element as a function of being able to consume a first compatible food element for a user with a given user body datum. In an embodiment, at least a server 104 may rank compatibility of at least a food element as a function of the at least a food compatibility index value. For instance, a food element with a high food compatibility index value may be ranked highly compatibly for a user as compared to a food element with a low food compatibility index value. In an embodiment, ranking at least a food element may include a hierarchical ranking that may rank food elements in decreasing and/or increasing level of compatibility.

With continued reference to FIG. 1, food element compatibility index value may be calculated as a function of at least a composition datum 108 and a first food element profile. First food element profile may include information describing a nutrient density score of a food element correlated to a given composition datum 108. Nutrient density may include a ranking and/or score reflecting the amount and/or quantity of vitamins, minerals, electrolytes, amino acids, antioxidants, micronutrients, fatty acids, and the like contained within a given food element and may be stored in a food element profile database 172 as described below in more detail in reference to FIG. 9. For example, an apple may have a high nutrient density score due to the Vitamin C, fiber, calcium, iron, Vitamin A, polyphenols, antioxidants and potassium contained with an apple as compared to a hot dog which may have a lower nutrient density score due to the presence of nitrates, excess sodium and sugar. In an embodiment, nutrient density scores may contain numerical values that may indicate the nutrient density of any given food element. In an embodiment, a high numerical nutrient density score may indicate a high amount of nutrients contained within a particular food element as compared to a low numerical nutrient density score which may indicate a low amount of nutrients contained within a particular food element. In an embodiment, nutrient density scores may be contained within a database operating on at least a server. In an embodiment, nutrient density scores may be calculated taking into account for example, absence of certain nutrients known to be beneficial such as vitamins and antioxidants as well as presence of certain nutrients that may not be as beneficial such as nitrates, preservatives and artificial ingredients for example.

With continued reference to FIG. 1, system 100 may include a supervised machine-learning module 176 operating on at least a server 104. Supervised machine-learning module 176 may select a training set from training set database 180 as described below in more detail in reference to FIG. 11. Supervised module is configured to select at least a first training set 184, create at least a supervised machine learning model 188 using the at least a first training set 184 wherein the at least a supervised machine learning model 188 relates body data to compatible food elements and generate at least a compatible food element as a function of the at least a composition datum 108 and the at least a first training set 184. With continued reference to FIG. 1, at least a server 104 may select at least a training set from training set database 180. Training set database 180 may contain training sets pertaining to different categories and classification of information, including training set components which may contain sub-categories of different training sets. In an embodiment, at least a server may select at least a first training set 184 by categorizing at least a composition datum 108 to contain at least a physiological label and select at least a first training set 184 as a function of the at least a physiological label. Physiological label, as used herein, includes any categorization and/or classification of a user body datum as belonging to a particular physiological categorization describing a user body datum as belonging to a particular body system. For example and without limitation, body system may include body dimensions which include classification by particular root cause pillars of disease. Dimension of the human body may include epigenetics, gut wall, microbiome, nutrients, genetics, and metabolism. In an embodiment, training set database 180 may contain training sets classified to body dimensions. In such an instance, training sets may be classified to more than one body dimension. For instance and without limitation, a training set may be classified to gut wall and microbiome. In yet another non-limiting example, a training set may be classified to nutrients and metabolism. First training set 184 may be selected by matching physiological label to a training set containing a matching physiological label. For example, a physiological label that contains microbiome may be matched to a training set containing a physiological label that contains microbiome. In an embodiment, first training set 184 may include the at least a correlated dataset.

With continued reference to FIG. 1, supervised machine learning model 188 may include without limitation model developed using linear regression models. Linear regression models may include ordinary least squares regression; which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Supervised machine-learning algorithms may include without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms; including convolutional neural net processes.

With continued reference to FIG. 1, supervised machine-learning algorithms may include using alternatively or additional artificial intelligence methods, including without limitation by creating an artificial neural network, such as a convolutional neural network comprising an input layer of nodes; one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using any training set as described herein; the trained network may then be used to apply detected relationships between elements of user input datums and antidotes.

Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below, Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance; natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grains containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

With continued reference to FIG. 1, at least a server 104 is designed and configured to generate at least a vibrant compatibility plan 192 wherein the at least a vibrant compatibility plan 192 further comprises a plurality of compatible food elements each containing at least a food element compatibility index value as a function of the at least a hierarchical clustering model 160. Vibrant compatibility plan 192, as used herein; includes any information and data containing a list of food elements each containing at least a food element compatibility index value. For example and without limitation, vibrant compatibility plan 192 may include a list of two hundred food elements each containing at least a food element compatibility index value. In an embodiment, two hundred food elements may be arranged in a hierarchical manner and ranked according to compatibility. For example, vibrant compatibility plan 192 may include a ranking in order of decreasing compatibility of two hundred food elements.

With continued reference to FIG. 1, at least a server 104 is configured to generate at least a vibrant compatibility plan 192 containing a sequencing instruction set wherein the sequencing instruction set contains at least an optimal combination of at least a first compatible food element and at least a second compatible food element as a function of the at least a desired dietary state. Sequencing instruction set may include information and/or data describing optimal combinations of foods and ingredients that a user may combine to create meals or that when combined together may optimize the nutrition of each other as a function of a user's desired dietary state. For instance and without limitation, sequencing instruction set may include information describing optimal combinations of a first compatible food element such as red kidney beans and a second compatible food element such as brown rice for a user with a desired dietary state of vegan diet. In yet another non-limiting example, sequencing instruction set may include information describing optimal combinations of a first compatible food element such as wild Alaskan salmon with a second compatible food element such as avocado for a user with a desired dietary state of ketogenic diet. In yet another non-limiting example, sequencing instruction set may include information describing optimal combinations of a first compatible food element such as bananas and a second compatible food element such as blueberries for a user with a desired dietary state of low FODMAP diet.

Figure 2:
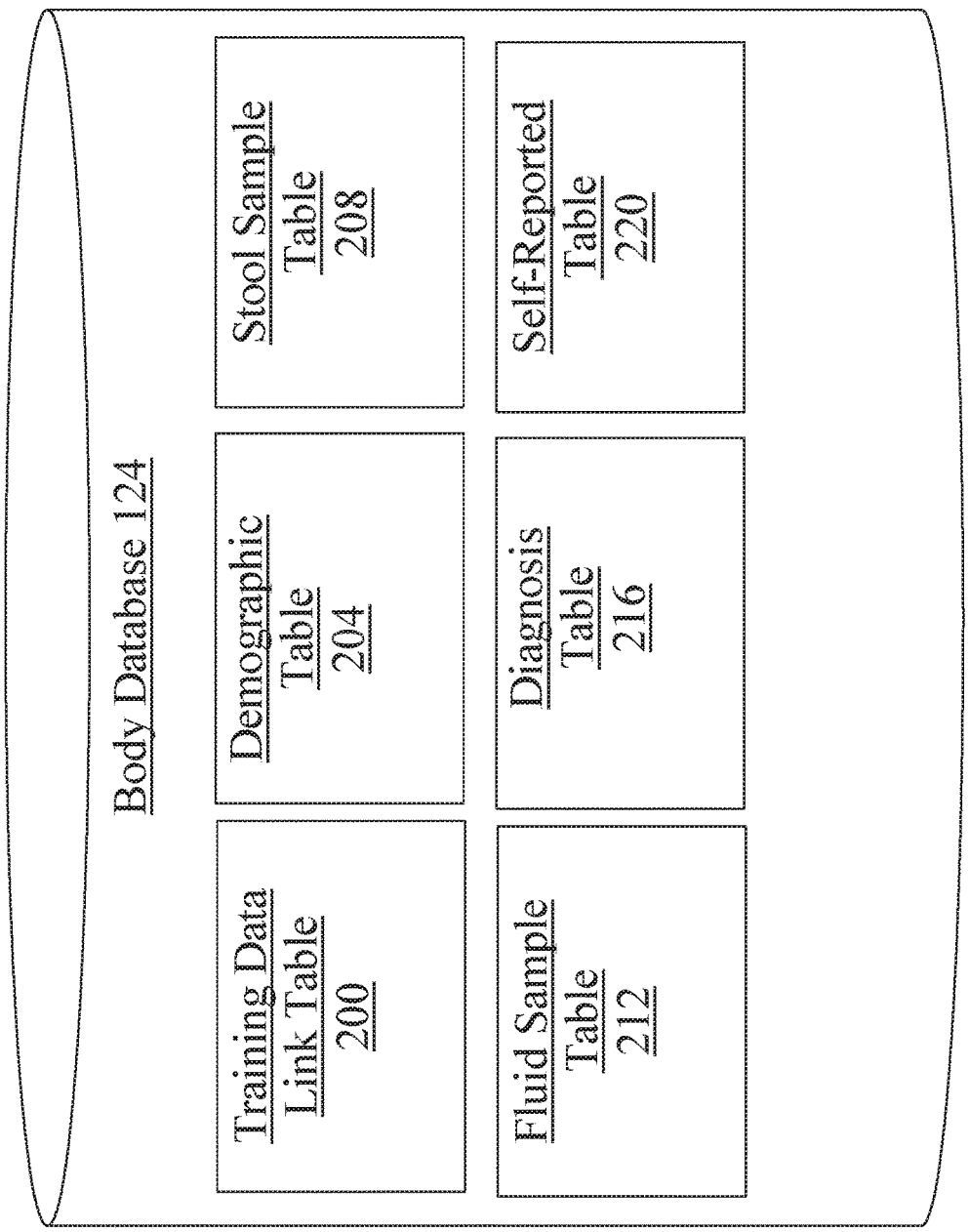
FIG. 2 is a block diagram illustrating an exemplary embodiment of a body database.

Referring now to FIG. 2, an exemplary embodiment of body database 124 is illustrated, which may be implemented, without limitation, as a hardware or software module. Body database 124 may be implemented, without limitation, as a relational database, a key-value retrieval datastore such as a NOSQL database, or any other format or structure for use as a datastore that a person skilled in the art would recognize as suitable upon review of the entirety of this disclosure. Body database 124 may contain datasets that may be utilized by unsupervised learning module 156 to find trends, cohorts, and shared datasets between data contained within body database 128 and composition datum 108. In an embodiment, datasets contained within body database 124 may be categorized and/or organized according to shared characteristics. For instance and without limitation, one or more tables contained within body database 124 may include training data link table 200; training data link table 200 may contain information linking datasets contained within body database 124 to datasets contained within training set database 180. For example, dataset contained within body database 124 may also be contained within training set database 180 which may be linked through training data link table 200. In yet another non-limiting example, training data link table 200 may contain information linking data sets contained within body database 124 to datasets contained within training set database 180 such as when dataset and training set may include data sourced from the same user or same cohort of users, or when dataset is utilized as training set. One or more tables contained within body database 124 may include demographic table 204; demographic table 204 may include datasets classified to demographic information. Demographic information may include datasets describing age, sex, ethnicity, socioeconomic status, education level, marital status, income level, religion, offspring information, and the like. One or more tables contained within body database 124 may include stool sample table 208; stool sample table 208 may include datasets classified to stool samples. Stool samples may include datasets describing stool levels of nutrition biomarkers including for example; measured values from a stool sample of anaerobes, parasites, firmicutes to Bacteroidetes ratio, absorption, inflammation, sensitivities, parasitology and the like. One or more tables contained within body database 124 may include fluid sample table 212; fluid sample table 212 may include datasets classified to fluid samples. Fluid samples may include datasets describing fluid samples analyzed for nutritional biomarkers including for example urine sample, semen sample, sweat sample, amniotic fluid sample, cerebrospinal fluid, synovial fluid sample, pleural fluid sample, pericardial fluid sample; blood sample, salivary sample, and the like. One or more tables contained within body database 124 may include diagnosis table 216; diagnosis table 216 may include datasets containing diagnostic information. Diagnostic information may include identification of an illness or health problem by a medical professional including for example, an informed advisor such as a functional medicine doctor, a nutritionist, an herbalist, an acupuncturist, a dietician, a nurse, and the like. One or more tables contained within body database 124 may include self-reported table 220; self-reported table 220 may include datasets containing self-reported nutritional states. Self-reported nutritional states may include for example, a user self-report to eliminate gluten due to bloating or a user self-report to eliminate meat for ethical reasons. One or more tables contained within body database 124 may include tissue sample table, nutrient biomarker table; chief complaint table, (not pictured). Persons skilled in the art will be aware of the various database tables that may be contained within body database 124 consistently within the purview of this disclosure.

Figure 3:
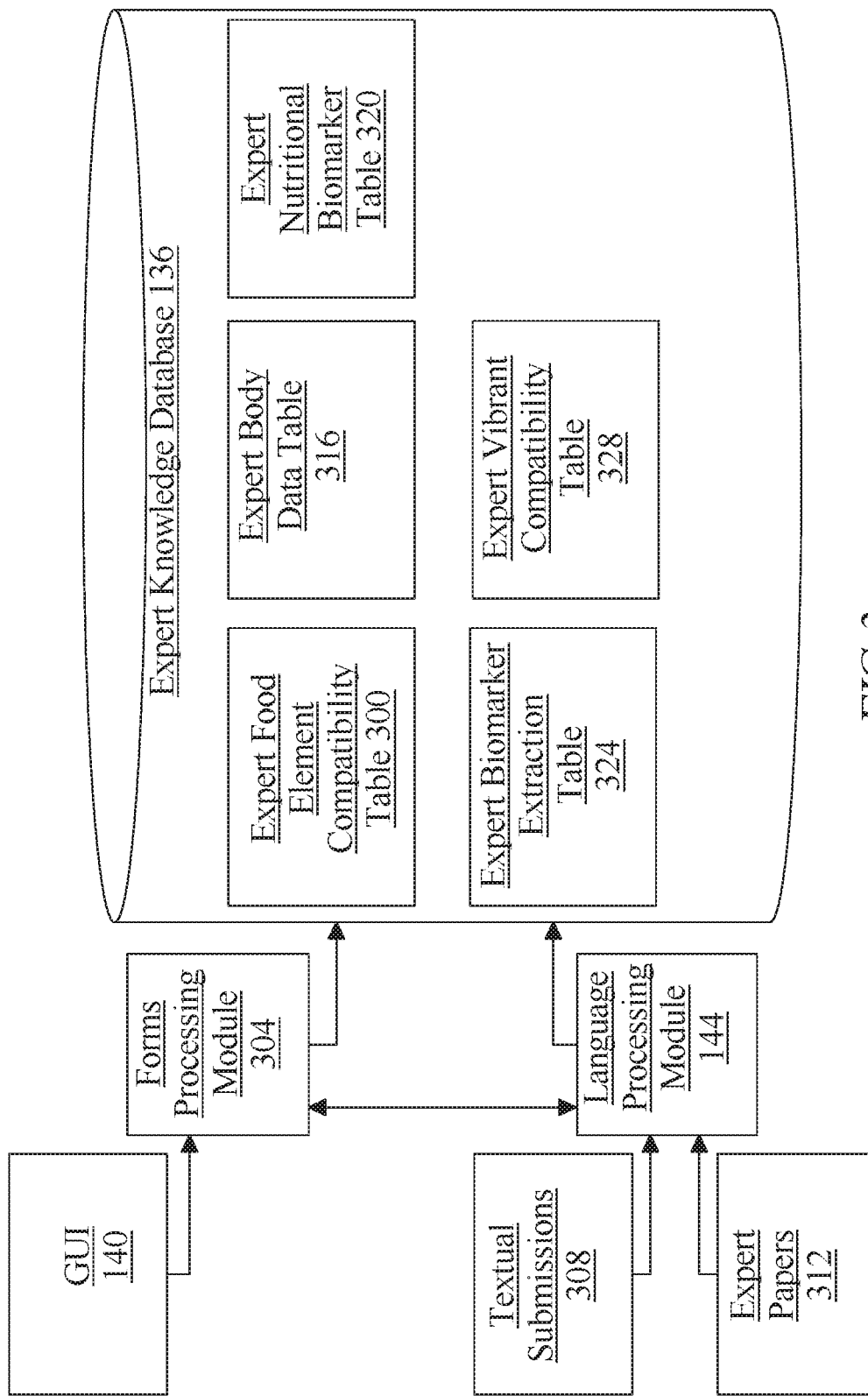
FIG. 3 is a block diagram illustrating an exemplary embodiment of an expert knowledge database.

Referring now to FIG. 3, an exemplary embodiment of expert knowledge database 136 is illustrated. Expert knowledge database 136 may include any data structure for ordered storage and retrieval of data, which may be implemented as a hardware or software module, and which may be implemented as any database structure suitable for use as body database 124. One or more database tables in expert knowledge database 136 may include, as a non-limiting example, an expert food element compatibility table 300. Expert food element compatibility table 300 may be a table relating user body data 116 to compatible food elements; for instance, where an expert has entered data relating a user body datum such as high triglycerides to a compatible food element such as oat bran, one or more rows recording such an entry may be inserted in expert food element compatibility table. In an embodiment, a forms processing module 304 may sort data entered in a submission via graphical user interface 140 by, for instance, sorting data from entries in the graphical user interface 140 to related categories of data; for instance, data entered in an entry relating in the graphical user interface 140 to a body datum may be sorted into variables and/or data structures for storage of body datums, while data entered in an entry relating to compatible food elements and/or an element thereof may be sorted into variables and/or data structures for the storage of, respectively, categories of compatible food elements. Where data is chosen by an expert from pre-selected entries such as drop-down lists, data may be stored directly; where data is entered in textual form, language processing module 144 may be used to map data to an appropriate existing label, for instance using a vector similarity test or other synonym-sensitive language processing test to map classified biomarker data to an existing label. Alternatively or additionally, when a language processing algorithm, such as vector similarity comparison, indicates that an entry is not a synonym of an existing label, language processing module 144 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 308, such as accomplished by filling out a paper or PDF form and/or submitting narrative information, may likewise be processed using language processing module 144. Data may be extracted from expert papers 312, which may include without limitation publications in medical and/or scientific journals, by language processing module 144 via any suitable process as described herein. Persons skilled in the art, upon reviewing the entirety of this disclosure, will be aware of various additional methods whereby novel terms may be separated from already-classified terms and/or synonyms therefore, as consistent with this disclosure, Expert food element compatibility table 300 may include a single table and/or a plurality of tables; plurality of tables may include tables for particular categories of food elements such as a vegetable table, a fruit table, an animal protein table, a seafood table, a spice table, a fat table, a grain table, and the like(not shown), to name a few non-limiting examples presented for illustrative purposes only.

With continued reference to FIG. 3, one or more database tables in expert knowledge database 136 may include, an expert body data table 316 may list one or more body datums as described by experts, and one or more compatible food products associated with body datum. For example, a body datum such as a blood test showing elevated glucose levels may be associated with one or more compatible food products such as animal protein, vegetables, and oils. As a further example an expert nutritional biomarker table 320 may list one or more nutritional biomarkers as described and input by experts and associated physiological classifications one or more nutritional biomarkers may be classified into as well as desired dietary state. For instance and without limitation, an expert biomarker table 320 may include one or more tables detailing biomarkers commonly associated with a particular diet such as Paleo diet or ketogenic diet and the like. In yet another non-limiting example, expert biomarker table 320 may include one or more tables detailing biomarkers commonly associated with a particular physiological system such as the gastrointestinal system or the neurological system. As an additional example, an expert biomarker extraction table 324 may include information pertaining to biological extraction and/or medical test or collection necessary to obtain a particular nutritional biomarker, such as for example a tissue sample that may include a urine sample, blood sample, hair sample, cerebrospinal fluid sample, buccal sample, sputum sample, and the like. As an additional example, an expert vibrant compatibility table 328 may include one or more tables detailing vibrant compatibility plan 192 associated with one or more elements of body data, biomarker data and the like. For example, expert vibrant compatibility table 328 may include information detailing hierarchies of compatible food elements for a particular body datum such as a body datum reflecting lactose intolerance may contain compatible food elements ranked as highly compatible to include buckwheat, amaranth, and celery ranked as highly compatible while cow yogurt, goat cheese, and cow milk may be ranked as being of very low compatibility. Tables presented above are presented for exemplary purposes only; persons skilled in the art will be aware of various ways in which data may be organized in expert knowledge database 136 consistently with this disclosure.

Figure 4:
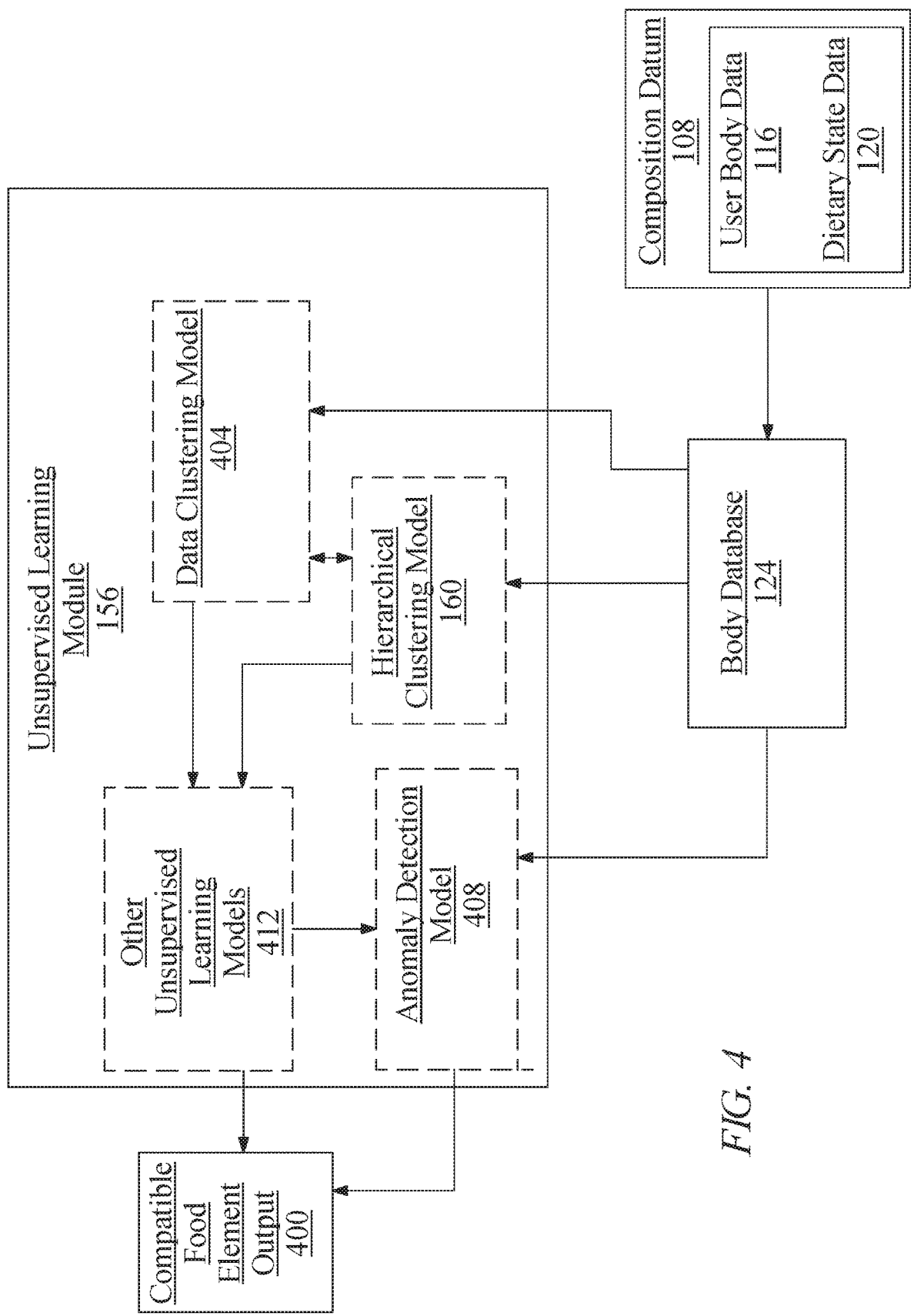
FIG. 4 is a block diagram illustrating an exemplary embodiment of an unsupervised learning module.

Referring now to FIG. 4, an exemplary embodiment of unsupervised learning module 156 is illustrated. Unsupervised learning may include any of the unsupervised learning processes as described herein, Unsupervised learning module 156 generates at least a hierarchical clustering model 160 to output at least a compatible food element 400 as a function of the at least a composition datum 108 and the at least a correlated dataset. Correlated dataset may be selected from body database 124 as described below in more detail in reference to FIG. 5, Body database 124 may contain data describing different users with different nutritional biomarkers and demographics of users, which may be organized into categories contained within body database 124 as described above in more detail in reference to FIG. 2. Hierarchical clustering model 160 may group and/or segment datasets into hierarchy clusters including both agglomerative and divisive clusters. Agglomerative clusters may include a bottom up approach where each observation starts in its own cluster and pairs of clusters are merged as one moves up the hierarchy. Divisive clusters may include a top down approach where all observations may start in one cluster and splits are performed recursively as one moves down the hierarchy. In an embodiment, hierarchical clustering model 160 may analyze datasets obtained from body database 124 to find observations which may each initially form own cluster. Hierarchical clustering model 160 may then identify clusters that are closest together and merge the two most similar clusters and continue until all clusters are merged together. Hierarchical clustering model 160 may output a dendrogram which may describe the hierarchical relationship between the clusters. Distance between clusters that are created may be measured using a suitable metric. Distance may be measured between for example the two most similar parts of a cluster known as single linkage, the two least similar bits of a cluster known as complete-linkage, the center of the clusters known as average-linkage or by some other criterion which may be obtained based on input received from expert knowledge database 136 for example.

With continued reference to FIG. 4, unsupervised learning module 156 may perform other unsupervised learning models to output at least a compatible food element output. Unsupervised learning module 156 may generate a data clustering model 404. Data clustering model 404 may group and/or segment datasets with shared attributes to extrapolate algorithmic relationships. Data clustering model 404 may group data that has been labelled, classified, and/or categorized. Data clustering model may identify commonalities in data and react based on the presence or absence of such commonalities. For instance and without limitation, data clustering model 404 may identify other data datasets that contain the same or similar nutritional biomarker contained within composition datum 108 or identify other datasets that contain users with similar demographics and/or background information. In an embodiment, data clustering model 404 may cluster data and generate labels that may be utilized as training set data. Data clustering model 404 may utilize other forms of data clustering algorithms including for example, hierarchical clustering, k-means, mixture models, OPTICS algorithm, and DBSCAN.

With continued reference to FIG. 4, unsupervised learning module 156 may generate an anomaly detection model 408. Anomaly detection model 408 may include identification of rare items, events or observations that differ significant from the majority of the data. Anomaly detection model 408 may function to observe and find outliers. For instance and without limitation, anomaly detect may find and examine data outliers such as a nutritional biomarker that is not compatible with any food elements or that is compatible with very few food elements.

With continued reference to FIG. 4, unsupervised learning module 156 may generate other unsupervised learning models 412. This may include for example, neural networks, autoencoders, deep belief nets, Hebbian learning, adversarial networks, self-organizing maps, expectation-maximization algorithm, method of moments, blind signal separation techniques, principal component analysis, independent component analysis, non-negative matrix factorization, singular value decomposition (not pictured).

Figure 5:
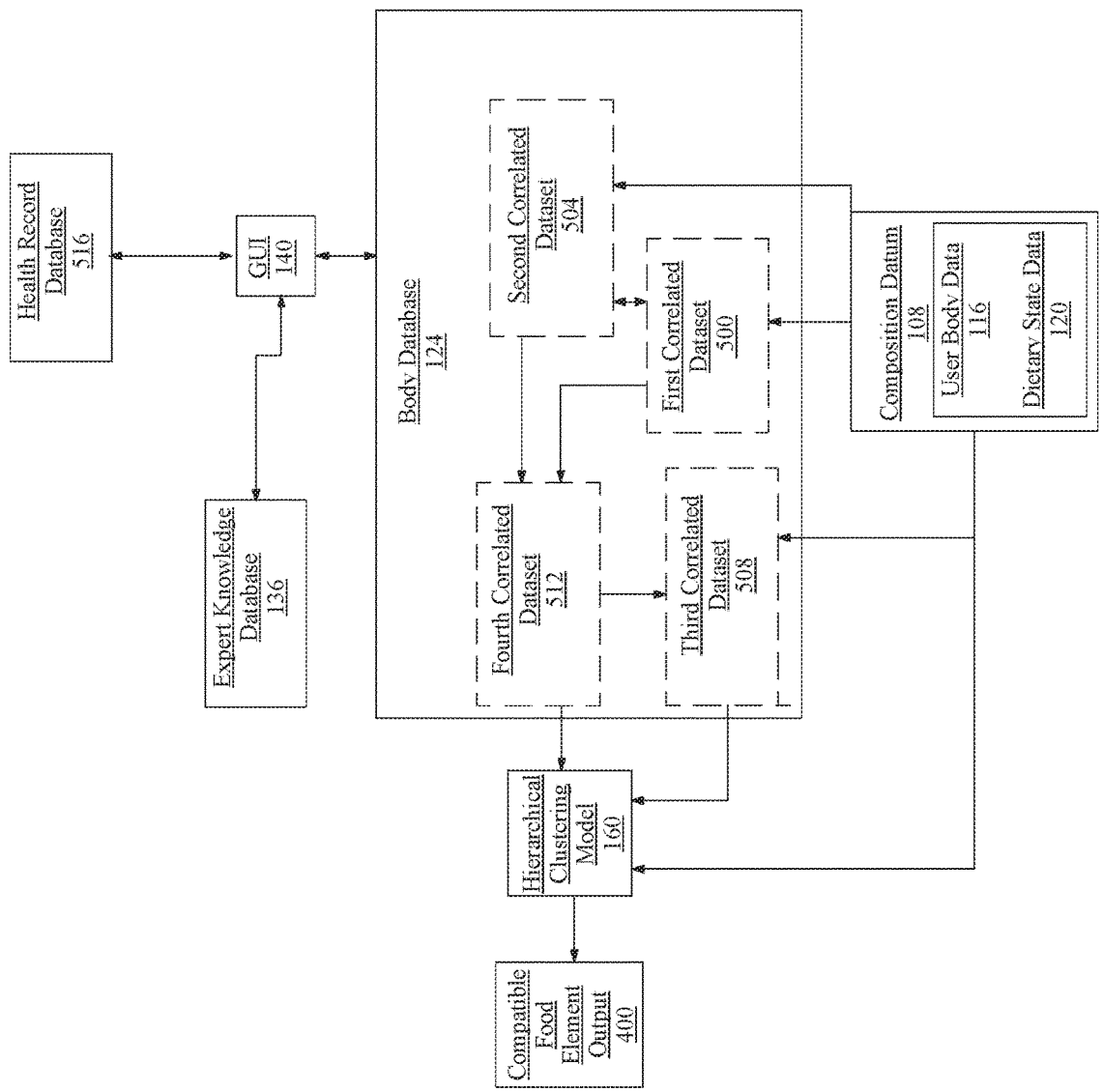
FIG. 5 is a block diagram illustrating an exemplary embodiment of a hierarchical clustering model.

Referring now to FIG. 5, an exemplary embodiment of hierarchical clustering model 160 is illustrated. Composition datum 108 containing an element of user body data 116 and an element of dietary state data 120 is utilized to select at least a correlated dataset from body database. In an embodiment, datasets contained within body database 124 may be organized into categories that each may be selected as a function of composition datum 108 as described above in more detail in reference to FIG. 2. For example, first correlated dataset 500 may be categorized as demographics and may contain datasets relating to demographics that may be utilized when generating hierarchical clustering model 160. In such an instance, second correlated dataset 504 may be categorized as fluid sample dataset that may contain datasets containing information relating to a particular nutritional biomarker extracted from a fluid sample that relates to fluid sample contained within user body data 116. In such an instance, third correlated dataset 508 may be categorized as diagnostic dataset, that may include contain data entries containing the same diagnosis as a user. In such an instance, fourth correlated dataset 512 may be categorized as socioeconomic dataset, that may contain data entries obtained from sources that are of a particular socioeconomic background related to user.

With continued reference to FIG. 5, datasets contained within body database may be obtained from a plurality of sources. Datasets contained within body database may be received from expert input such and contained within expert knowledge database 136 as described above in more detail in reference to FIG. 3. In an embodiment, experts such as leading functional medicine practitioners and scientists may provide input through GUI 140 whereby such information may be contained within expert knowledge database 136. Datasets contained within body database 124 may also be obtained from health record database 516, which may contain datasets obtained from different sources such as deidentified medical records as described below in more detail in reference to FIG. 6. Datasets selected from body database 124 by at least a server 104 may be utilized in combination with composition datum 108 to generate hierarchical clustering model 160. Hierarchical clustering model 160 outputs at least a compatible food element. Compatible food element includes any of the compatible food elements as described herein.

Figure 6:
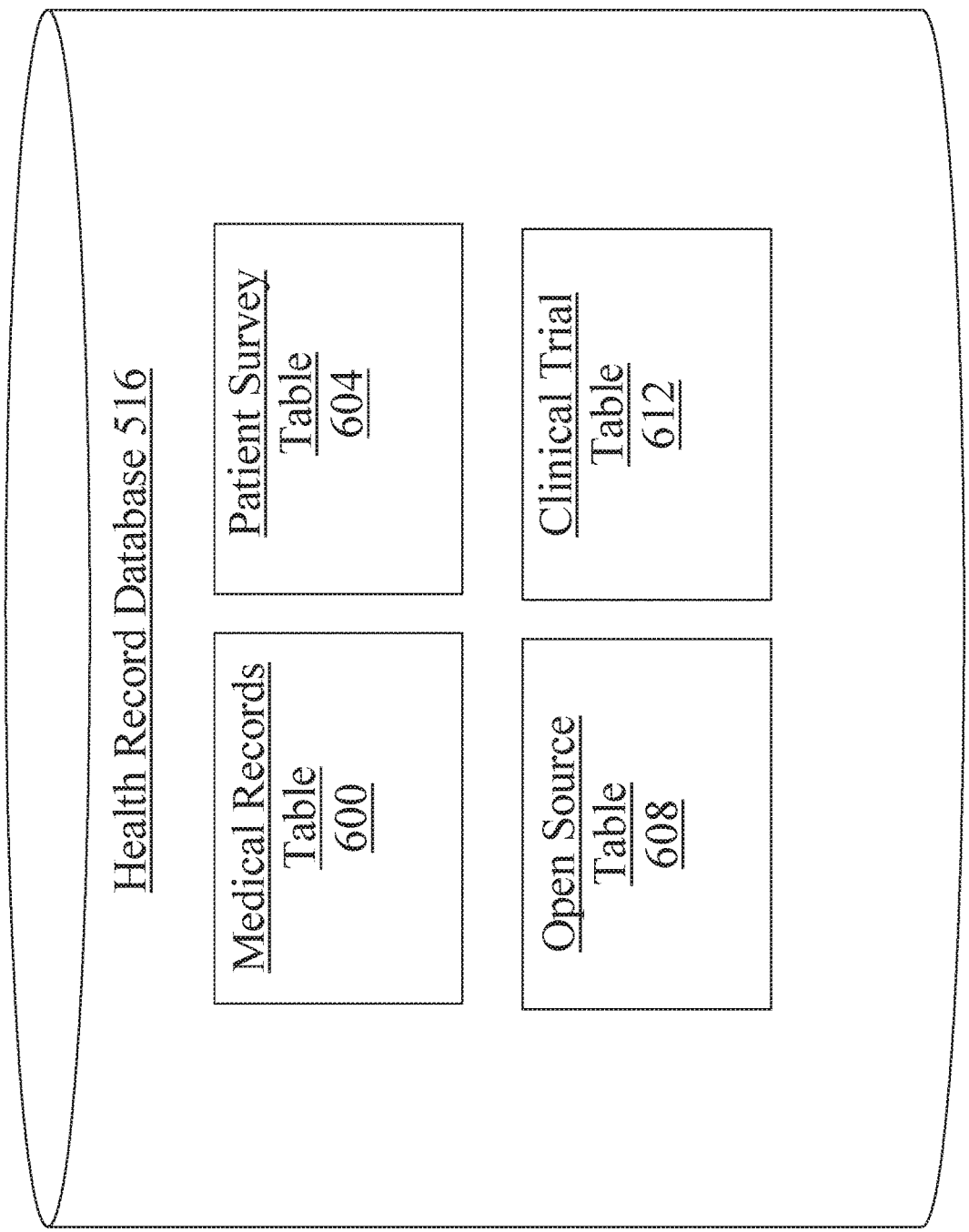
FIG. 6 is a block diagram illustrating an exemplary embodiment of a health record database.

Referring now to FIG. 6, an exemplary embodiment of health record database 516 is illustrated. Health record database 516 may include any data structure for ordered storage and retrieval of data, which may be implemented as a hardware or software module, and which may be implemented as any database structure suitable for use as body database 124. Health record database 516 may include datasets input from a plurality of sources that may be used as datasets by body database 124 and/or training set database 180. One or more tables contained within health record database 516 may include, as a non-limiting example, medical records table 600; medical records table 600 may include data obtained from medical records. Medical records table 600 may include medical record data that may be sourced from physicians, electronic health records, hospitals, nursing homes, skilled nursing facilities, health insurance companies and the like. One or more tables contained within health record database 516 may include, as a non-limiting example, patient survey table 604; patient survey table 604 may include data obtained from patient surveys. Patient survey table 604 may include patient surveys obtained from patients in specific geographic areas, specific socioeconomic backgrounds, patients with particular health problems, and the like. One or more tables contained within health record database 516 may include, as a non-limiting example, open source table 608; open source table 608 may include data obtained from open sources. Open source table 608 may include data obtained from open sources such as government sources and websites that may contain data available for use by anyone. One or more tables contained within health record database 516 may include, as a non-limiting example, clinical trial table 612; clinical trial table 612 may include data obtained from clinical trials. Clinical trial table 612 may include information obtained for example from clinical trials at research centers and academic institutions.

Figure 7:
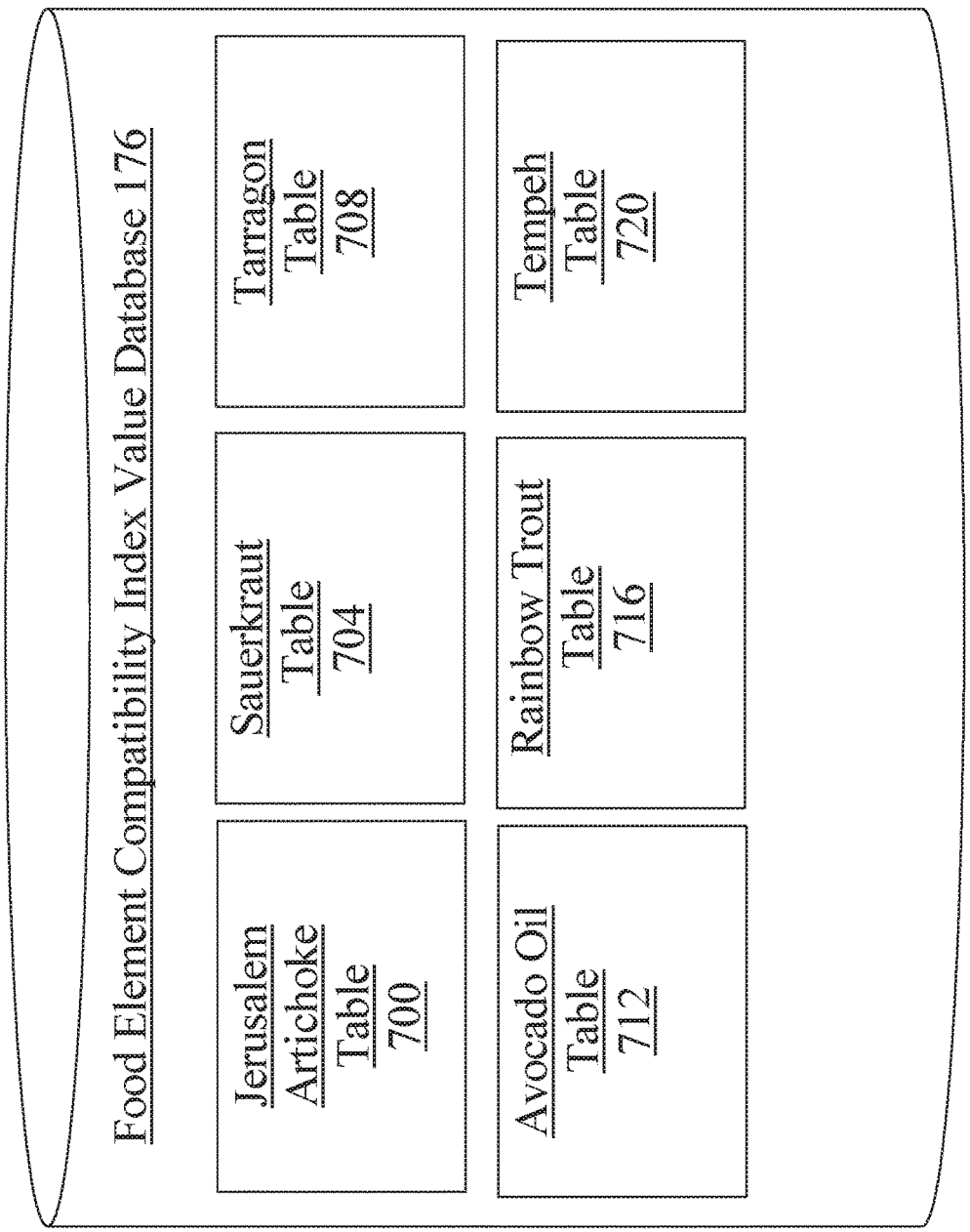
FIG. 7 is a block diagram illustrating an exemplary embodiment of a food element compatibility index value database.

Referring now to FIG. 7, an exemplary embodiment of food element compatibility index value database 168 is illustrated. Food element compatibility index value database 168 may include any data structure for ordered storage and retrieval of data, which may be implemented as a hardware or software module, and which may be implemented as any database structure suitable for use as body database 124. Food element compatibility index value database 168 may contain information describing compatible substance index values for individual food elements. Food element compatibility index value database 168 may be consulted by at least a server 104 when generating at least a vibrant compatibility plan 192. Food element compatibility index value database 168 may be consulted by at least a server 104 when ranking food elements. Food element compatibility index value database 168 may contain food element compatibility index value for individual food elements and each compatibility index value for each food linked to a particular body datum, nutritional biomarker, and/or dietary state. Food element compatibility index value database 168 may also contain food element compatibility index values for combinations of multiple food elements and compatibility of a second compatibility food element as a function of selecting a first compatibility food element based on food element compatibility index value as described above in more detail in reference to FIG. 1. One or more database tables contained within food element compatibility index value database 168 may include Jerusalem artichoke table 700; Jerusalem artichoke table 700 may include compatibility index values for Jerusalem artichoke for any given nutritional biomarker, body datum, and compatibility index values for Jerusalem artichoke as compared to other compatible food elements for any given biomarker and/or body datum. For example, Jerusalem artichoke may have a high compatibility index value for a biomarker that shows low gastrointestinal levels of *Streptococcus* and *Lactobacillus* but may have a low compatibility index value for a biomarker that shows overgrowth of *Candida*. One or more database tables contained within food element compatibility index value database 168 may include sauerkraut table 704; sauerkraut table 704 may include compatibility index values for sauerkraut for any given nutritional biomarker, body datum, and compatibility index values for sauerkraut as compared to other compatible food elements for any given biomarker and/or body datum. For example and without limitation, sauerkraut may have a high compatibility index value for a dietary state such as paled but may have a low compatibility index value for a dietary state such as yeast-free diet. One or more database tables contained within food element compatibility index value database 168 may include tarragon table 708; tarragon table 708 may include compatibility index values for tarragon for any given nutritional biomarker, body datum, and compatibility index values for tarragon as compared to other compatible food elements for any given biomarker and/or body datum. One or more database tables contained within food element compatibility index value database 168 may include avocado oil table 712; avocado oil 712 may include may include compatibility index values for avocado oil for any given nutritional biomarker, body datum, and compatibility index values for avocado as compared to other compatible food elements for any given biomarker and/or body datum. For example, avocado oil may contain a high compatibility index value when substituted to selected as a function of an avocado. One or more database tables contained within food element compatibility index value database 168 may include rainbow trout table 716; rainbow trout table 716 may include may include compatibility index values for rainbow trout for any given nutritional biomarker, body datum, and compatibility index values for avocado as compared to other compatible food elements for any given biomarker and/or body datum. For example, rainbow trout may have a high compatibility index value as compared to compatibility index value for brown trout, indicating a high likelihood that rainbow trout may be substituted and/or selected as a function first selecting brown trout. One or more database tables contained within food element compatibility index value database 168 may include tempeh table 720; tempeh table 720 may include compatibility index values for tempeh for any given nutritional biomarker, body datum, and compatibility index values for avocado as compared to other compatible food elements for any given biomarker and/or body datum. For example, tempeh may contain a high compatibility index value for a dietary state such as vegan diet but a low compatibility index value for a dietary state such as ketogenic. Tables contained within food element compatibility index value database may include other foods including for example, chestnuts; coffee, cantaloupe melon, pistachios, arugula, bamboo shoots, beet greens, broccoli, burdock root, Italian artichoke, asparagus, beet, bok choy, Brussel sprouts, cabbage, celery (not picture). Persons skilled in the art upon reviewing the entirety of this disclosure, will be aware of various forms which may be suitable for use as compatibility index value database consistently with this disclosure.

Referring now to FIG. 8, an exemplary embodiment of Jerusalem artichoke table 700 is illustrated. For instance and without limitation, Jerusalem artichoke table 700 may contain individual compatibility index value scores for Jerusalem artichoke as compared to other biomarkers, body datums, dietary states, and food elements. For instance and without limitation, Jerusalem artichoke table 700 may contain a first column 800 containing other biomarkers, body datums, dietary states, and food elements. For instance and without limitation, Jerusalem artichoke table 700 may contain a second column 804 containing the specific compatibility index value for a Jerusalem artichoke for the particular item of comparison located in column 1 800. For instance and without limitation, Jerusalem artichoke table 700 may contain a first nutritional biomarker 808 and a compatibility index value 812 for a Jerusalem artichoke linked to first nutritional biomarker 808. For instance and without limitation, Jerusalem artichoke table 700 may contain a first body datum 816 and a compatibility index value 820 for a Jerusalem artichoke linked to first body datum 816. For instance and without limitation, Jerusalem artichoke table 700 may contain a first dietary state 824 and a compatibility index value 828 for a Jerusalem artichoke linked to first dietary state 824. For instance and without limitation, Jerusalem artichoke table 700 may contain a first food element 832 and a compatibility index value 836 for a Jerusalem artichoke linked to first food element 832. In an embodiment, Jerusalem artichoke table 700 may contain n entries of nutritional biomarkers, n entries of body datums, n entries of dietary states, and n entries of food elements. In an embodiment, each food element may contain a table listing compatibilities of each food element to each item contained within column 1 to compatibility index values contained within column 2 as described above in reference to FIG. 7.

Figure 9:
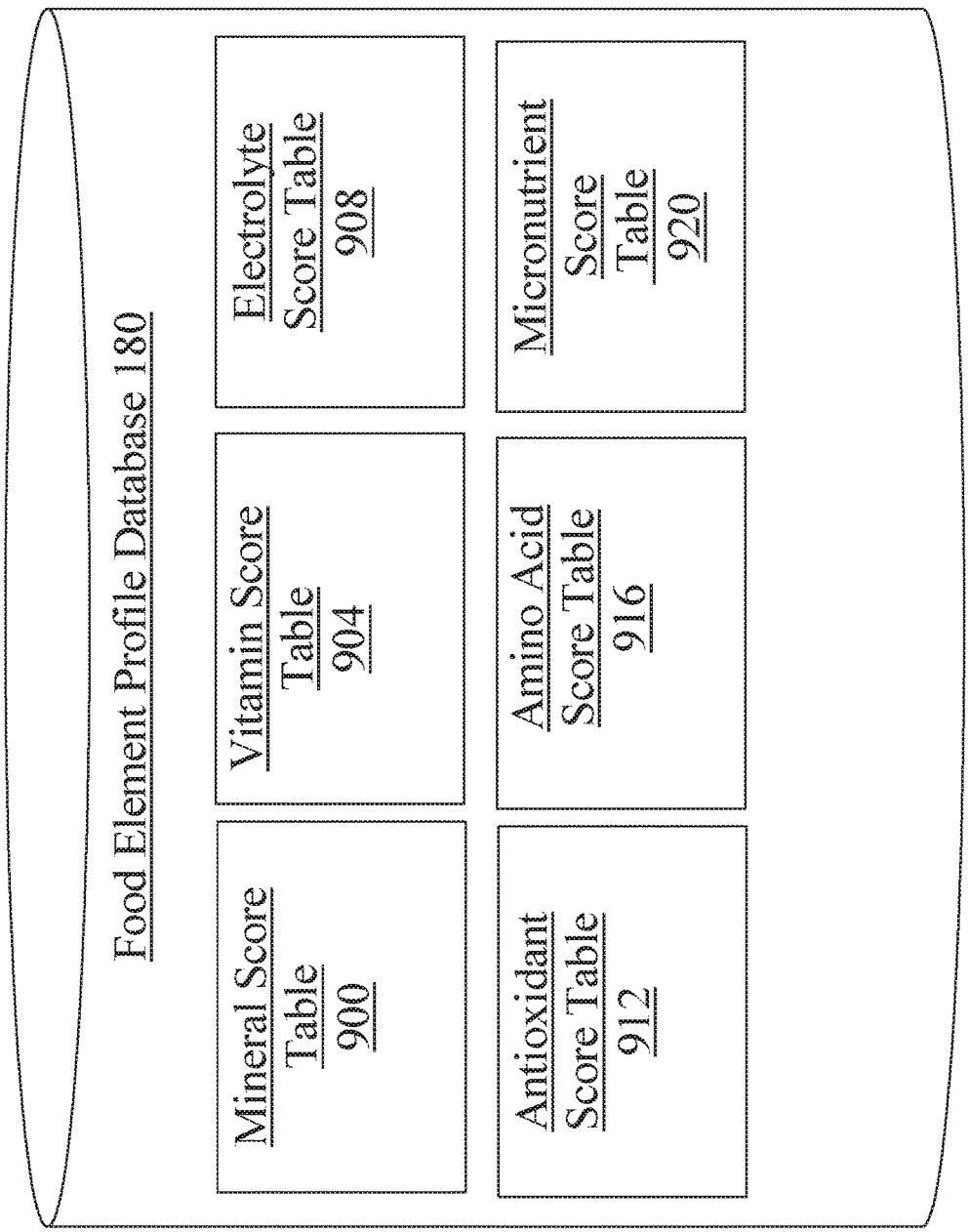
FIG. 9 is a block diagram illustrating an exemplary embodiment of a food element profile database.

Referring now to FIG. 9, an exemplary embodiment of food element profile database 172 is illustrated. Food element profile database 172 may include any data structure for ordered storage and retrieval of data, which may be implemented as a hardware or software module, and which may be implemented as any database structure suitable for use as body database 124. Food element profile database 172 may contain information containing nutrient density information about a particular food element. Data contained within food element profile database 172 may be utilized to calculate food element compatibility index value and when generating vibrant compatibility plan 192t. One or more tables contained within food element profile database 172 may include for instance mineral score table 900; mineral score table 900 may include information describing minerals contained within a particular food element. For example, mineral score table 900 may include minerals such as iron and calcium contained within a particular food element such as a banana or minerals contained within multiple food elements such as for example orange cantaloupe melon, chicken, and black lentils. One or more tables contained within food element profile database 172 may include for instance, vitamin score table 904; vitamin score table 904 may include information describing vitamins contained within a particular food element. For example, vitamin score table 904 may include vitamins such as Vitamin C, Vitamin E, and Vitamin D contained within one or more food elements such as blackstrap molasses, buckwheat, and oatmeal. One or more tables contained within food element profile database 172 may include for instance, electrolyte score table 908; electrolyte score table may include information describing electrolytes contained within a particular food element. For example, electrolyte score table 908 may include information describing electrolyte quantities such as potassium, and sodium contained within a food element such as lamb or walnuts. One or more tables contained within food element profile database 172 may include for instance, antioxidant score table 912; antioxidant score table 912 may include information describing antioxidants contained within a particular food element and/or plurality of food elements. For example, antioxidant table 912 may include information describing antioxidants that may aid in slowing oxidation or electron transfer such as for example cranberries, blueberries, grapes, raspberry, elderberry, black currants, pomegranates, plums and the like. One or more tables contained within food element profile database 172 may include for instance, amino acid score table 916; amino acid score table 916 may include information describing amino acids contained within a particular food element. For example, amino acid score table 916 may include information describing amino acids contained within a particular food element including for example amino acids such as valine, alanine, arginine, glutamine, lysine, aspartic acid, glutamic, acid and the like. For example, amino acid score table 916 may include information describing quantities of amino acids such as valine and leucine contained within white turkey or quantities of lysine and aspartic acid contained within tofu. One or more tables contained within food element profile database 172 may include for instance, micronutrient score table 920; micronutrient score table 920 may include information describing quantities of micronutrients contained within a particular food element. For example, micronutrient score table 920 may include information describing quantities of folate and iodine contained within a particular food element. Information contained within food element profile database 172 may include other score tables including for example, metabolites, fatty acids, fat content, saturated fat content, protein content, carbohydrate content, (not pictured) and the like. Persons skilled in the art upon reviewing the entirety of this disclosure, will be aware of various forms which may be suitable for use as food element profile database 172 consistently with this disclosure.

Figure 10:
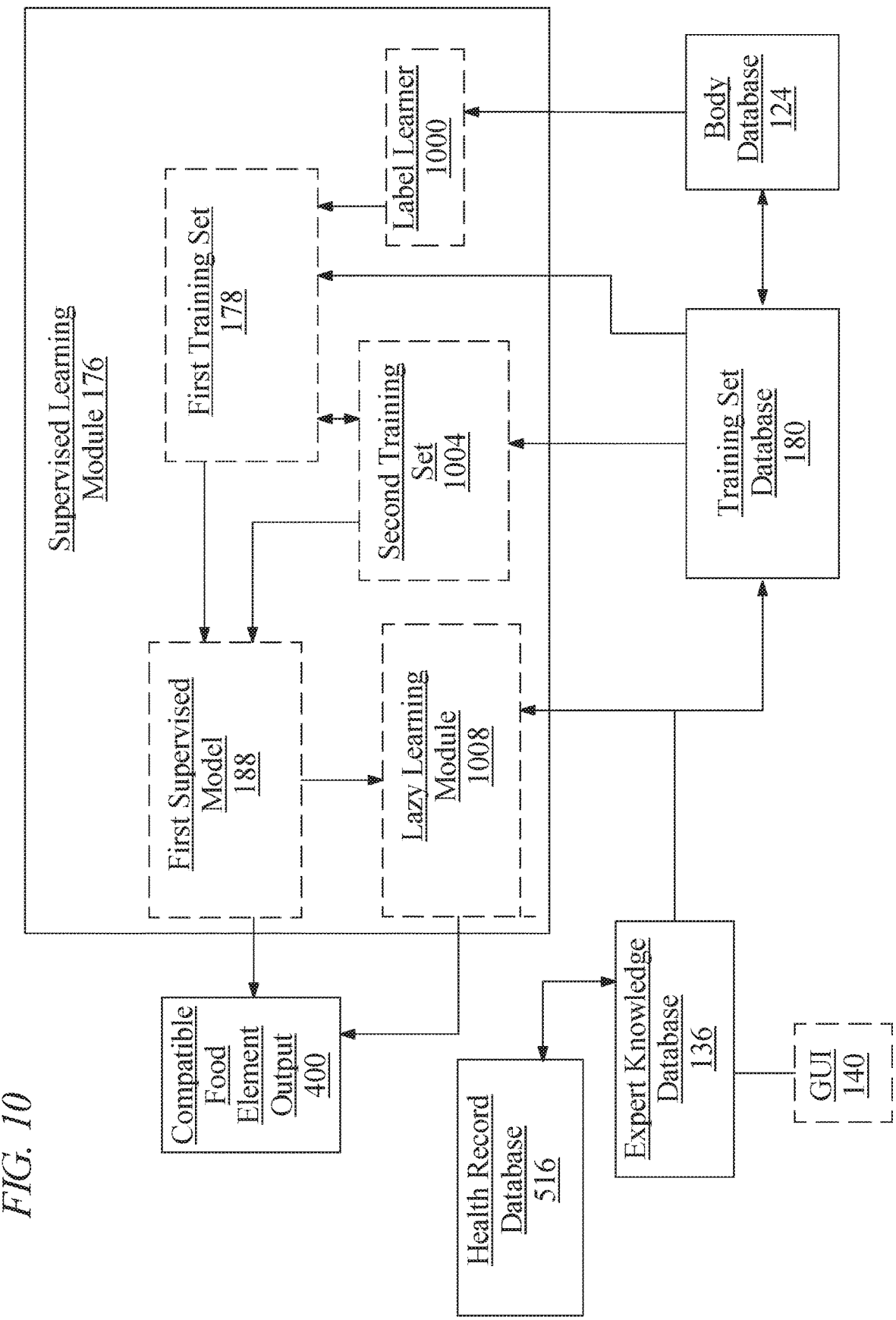
FIG. 10 is a block diagram illustrating an exemplary embodiment of a supervised learning module.

Referring now to FIG. 10, an exemplary embodiment of supervised learning module 176 is illustrated. Supervised learning module 176 may include at least a label learner 1000 designed and configured to create at least a supervised machine learning model 188 using the at least a first training set 184 wherein the at least at supervised machine learning model 188 relates body data to compatible food elements. First training set 184 may be selected from training set database 180. Supervised learning module 176 may be configured to perform any supervised machine-learning algorithm as described above in reference to FIG. 1, This may include for example, support vector machines, linear regression, logistic regression, naïve Bayes, linear discriminant analysis, decision trees, k-nearest neighbor algorithm, neural networks, and similarity learning. Supervised machine-learning module may generate a first supervised machine learning model 188 which may be utilized to generate compatible food element output 400. In an embodiment, first training set 184 may include the at least a correlated dataset. First training set 184 may be selected by categorizing the at least a user body datum to contain at least a physiological label and select at least a first training set 184 as a function of the at least a physiological label. In an embodiment, training sets contained within training set database 180 may be organized and categorized by groupings of physiological labels as described in more detail below in reference to FIG. 11.

With continued reference to FIG. 10, supervised learning module 176 may include at least a label learner 1000 which may include any hardware or software module. At least a label learner 1000 may select first training set 184 and/or second training set 1004 from training set database 180 and/or body database 124. In an embodiment, at least a label learner 1000 may generate different supervised models 186 to create learned associations between training sets and inputs and outputs utilized to select training sets such as correlations between body data and correlated compatible food elements. In an embodiment, at least a label learner 1000 may select datasets from body database 124 to be utilized as training sets. Datasets contained within body database 124 and/or training set database 180 may be generated based on inputs by experts and sources contained within expert knowledge database 136 and/or health record database 516 through submissions generated by experts at graphical user interface 140.

With continued reference to FIG. 10, supervised learning module 176 may generate compatible food element output 400 by executing a lazy learning module 1008 as a function of a user body datum and a compatible food element output 400. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at an antidote associated with at least a user input datum, using at least a training set. As a non-limiting example, an initial heuristic may include a ranking of compatible food elements according to relation to a test type of at least a user body datum, one or more categories of body data identified in test type of at least a composition datum 108, and/or one or more values detected in at least a user composition datum 108 sample; ranking may include, without limitation, ranking according to significance scores of associations between elements of body data and compatible food elements, for instance as calculated as described above. Heuristic may include selecting some number of highest-ranking associations and/or compatible food elements. Lazy learning module 1008 may alternatively or additionally implement any suitable "lazy learning" algorithm, including without limitation a K-nearest neighbors algorithm, a lazy naïve Bayes algorithm; or the like; persons skilled in the art; upon reviewing the entirety of this disclosure, will be aware of various lazy-learning algorithms that may be applied to generate antidotes as described in this disclosure, including without limitation lazy learning applications of machine-learning algorithms as described in further detail below.

Figure 11:
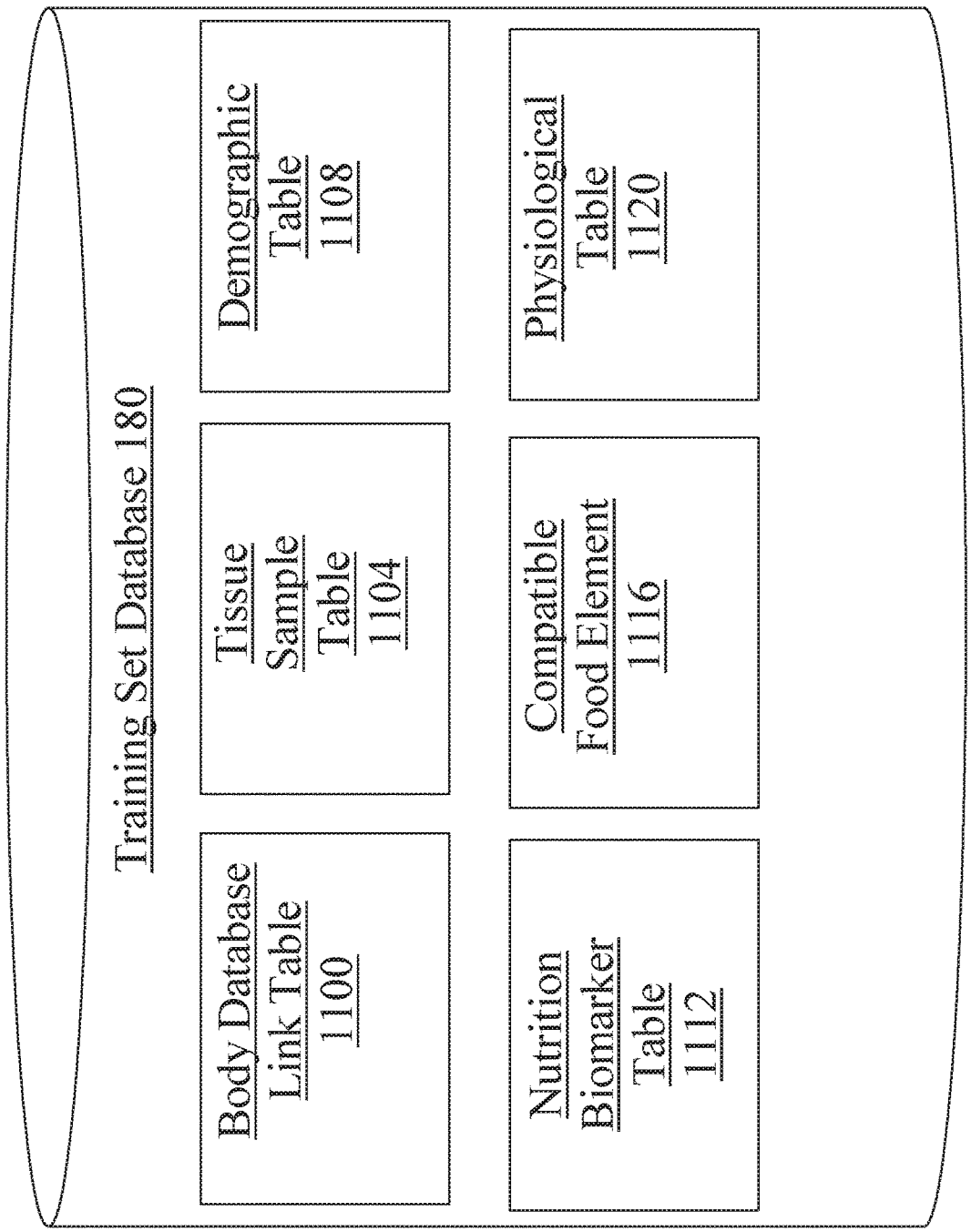
FIG. 11 is a block diagram illustrating an exemplary embodiment of a training set database.

Referring now to FIG. 11, an exemplary embodiment of training set database 180 is illustrated. Training set database 180 may include any data structure for ordered storage and retrieval of data, which may be implemented as a hardware or software module, and which may be implemented as any database structure suitable for use as body database 124. For instance and without limitation, one or more database tables contained within training set database 180 may include body database link table 1100; body database link table 1100 may contain information linking datasets contained within body database. For example, dataset contained within body database may also be contained within training set database 180 which may be linked through body database link table 1100. In yet another non-limiting example, body database link table 1100 may contain information linking datasets contained within body database to datasets contained within training set database 180, such as when dataset and training set may include data sourced from the same user or same cohort of users. For instance and without limitation, one or more database tables contained within training set database 180 may include tissue sample table 1104; tissue sample table 1104 may contain training sets containing tissue samples that may contain one or more nutritional biomarkers which may be correlated to one or more compatible food element outputs. Tissue sample table 1104 may include tissue samples such as blood, cerebrospinal fluid, urine, blood plasma, synovial fluid, amniotic fluid, lymph, tears, saliva, semen, aqueous humor, vaginal lubrication, bile, mucus, vitreous body, gastric acid, which may be correlated to a compatible food element output. For instance and without limitation, one or more database tables contained within training set database 180 may include demographic table 1108; demographic table 1108 may contain training sets containing demographics that may contain body data and one or more demographics correlated to one or more compatible food element outputs. Demographics may include residence location, geographical area where a subject may live, age, race, ethnicity, gender, marital status, income, education, employment and the like. For instance and without limitation, one or more database tables contained within training set database 180 may include nutrition biomarker table 1112; nutrition biomarker table 1112 may include one or more nutrition biomarkers correlated to one or more compatible food elements. For example, a nutrition biomarker contained within a training set may contain a biomarker such as *Candida* overgrowth in the gastrointestinal tract correlated to a compatible food such as spinach. For instance and without limitation, one or more database tables contained within training set database 180 may include compatible food element table 1116; compatible food element table 116 may include compatible food elements correlated to other compatible food elements. For example, compatible food element table 1116 may include a first compatible food element correlated to a second compatible food element. For instance and without limitation, one or more database tables contained within training set database 180 may include physiological table 1120; physiological table 1120 may include one or more physiological labels correlated to one or more compatible food elements. For example, physiological table 1120 may include a physiological label such as neurological correlated to one more compatible food elements containing B Vitamins such as buckwheat, oats, amaranth, and barley. Persons skilled in the art upon reviewing the entirety of this disclosure, will be aware of various forms which may be suitable for use as training set database 180 consistently with this disclosure.

Figure 12:
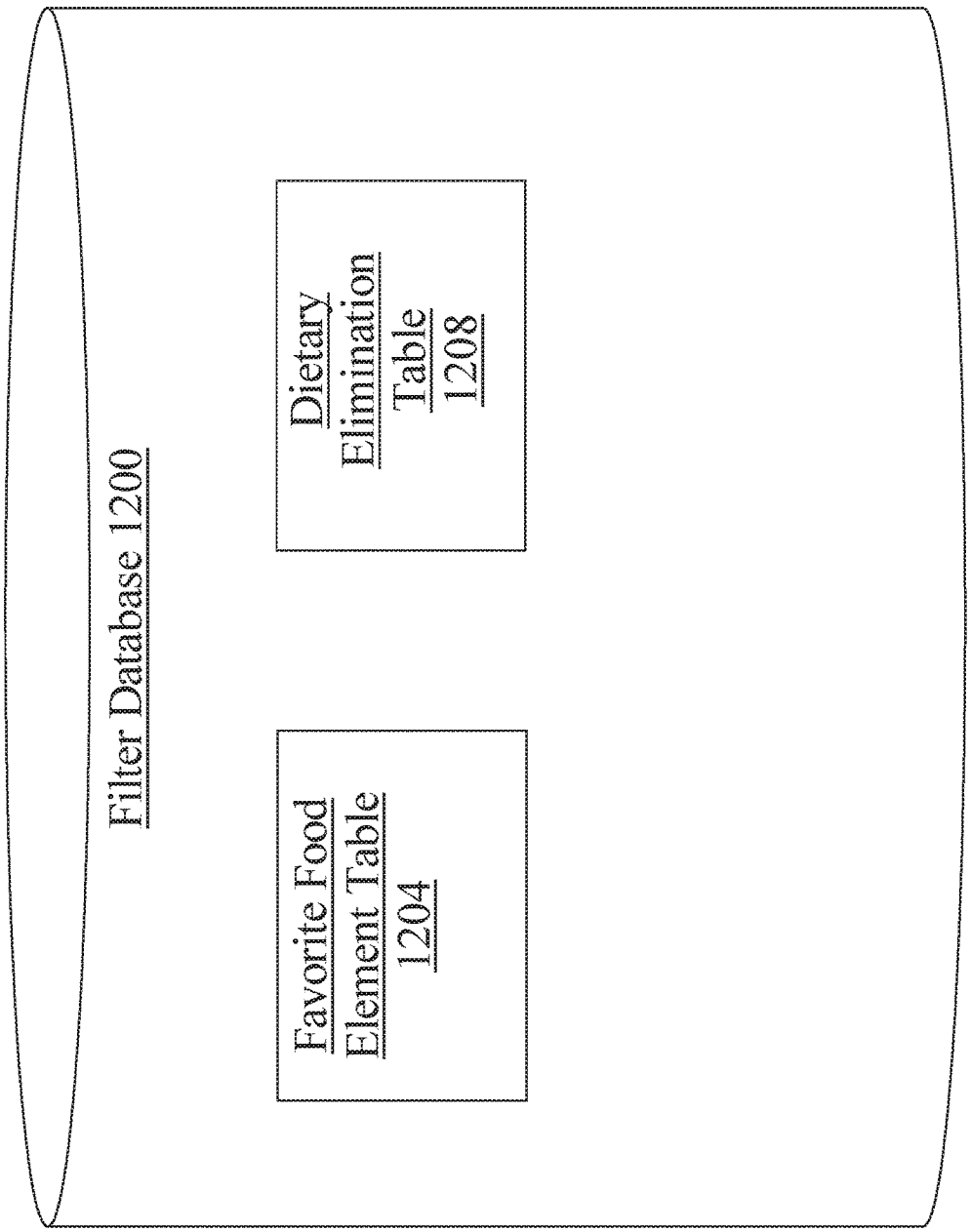
FIG. 12 is a block diagram illustrating an exemplary embodiment of a filter database.

Referring now to FIG. 12, an exemplary embodiment of filter database 1200 is illustrated. Filter database 1200 may include any data structure for ordered storage and retrieval of data, which may be implemented as a hardware or software module, and which may be implemented as any database structure suitable for use as body database 124. Filter database 1200 may include information input by user regarding user's favorite food elements and dietary restrictions. Filter database 1200 may be consulted by at least a server 104 when generating at least a vibrant compatible plan to filter off compatible food elements that may not match a user's food and eating preferences. One or more tables contained within filter database 1200 may include favorite food element table 1204; favorite food element table 1204 may include a user's preference for favorite food elements. For example, favorite food element table 1204 may include the top ten food elements that a user consumes on a weekly basis for instance. One or more tables contained within filter database 1200 may include dietary elimination table 1208; dietary elimination table 1208 may include information pertaining to a particular food element or food group that a user may need to eliminate due to a user's own personal preference to not consume a particular food element for ethical or moral reasons or due to an allergy such as an anaphylactic allergy to a food element such as tree nuts or dairy products. Persons skilled in the art upon reviewing the entirety of this disclosure, will be aware of various forms which may be suitable for use as filter database consistently with this disclosure.

Figure 13:
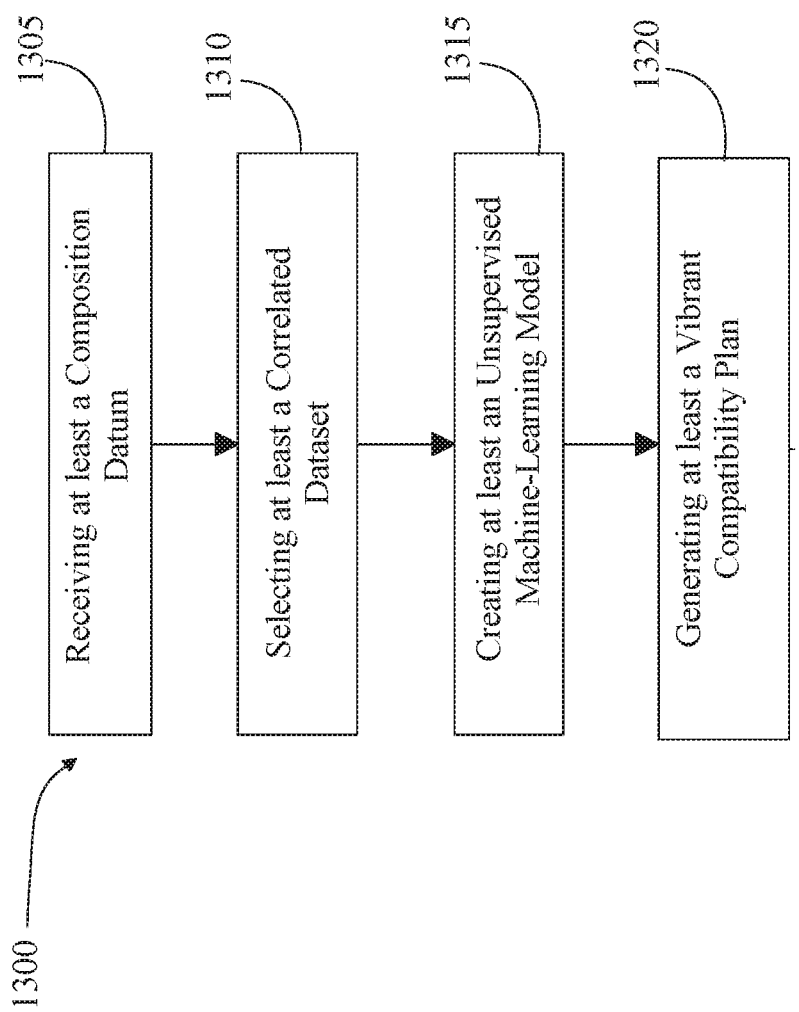
FIG. 13 is a process flow diagram illustrating an exemplary embodiment of a method of generating a vibrant compatibility plan using artificial intelligence.

Referring now to FIG. 13, an exemplary embodiment of a method 1300 of generating a dietary state plan using artificial intelligence is illustrated. At step 1305 at least a server 104 receives at least a composition datum 108 from a user client device 112 generated as a function of at least a user conclusive label and at least a user dietary response wherein the at least a composition datum 108 further comprises at least an element of user body data 116 and at least an element of desired dietary state data. At least a composition datum 108 may be received by at least a server 104 utilizing any of the network methodology as described herein. At least a composition datum 108 may include any of the composition datum 108 as described herein. At least an element of user body data 116 may include any of the user body data 116 as described herein. For example, at least an element of user body data 116 may include a nutritional biomarker such as for example a genotype marking of the ACE gene that regulates blood pressure. In an embodiment, at least an element of user body data 116 may include a user self-reported elimination of a particular food element such as for example, a user's self-reported elimination of gluten products due to bloating or a user's self-reported elimination of dairy containing products due to lose stools. At least an element of desired dietary state data 120 may include any of the dietary state data 120 as described herein. For example, at least an element of desired dietary state data 120 may include a user's desire or current diet that consists of the paleo diet or a vegan diet. In an embodiment, at least an element of body data and at least an element of desired dietary state data 120 may include the same inputs. For example, at least a composition datum 108 may include at least an element of user body data 116 that includes a user's self-reported elimination of all animal containing food products and at least an element of desired dietary state data 120 that includes a current diet of a vegan diet which does not contain any animal products. In yet another non-limiting example, at least a composition datum 108 may include a user's self-reported elimination of all grain containing foods and at least an element of desired dietary state data 120 that includes a description of a desire to consume a paleo diet. At least a composition datum may be generated as a function of at least a user conclusive label and at least a user dietary response. This may be done utilizing any of the methodologies as described above in reference to FIG. 1. For example, at least a user conclusive label such as a diagnosis of heart disease may be utilized to generate at composition datum that includes body data such as an elevated lipid panel and desired dietary state data that includes a low-fat diet. In yet another non-limiting example, at least a user dietary response such as a preference for gluten free foods due to stomach bloating and cramping may be utilized by a user to generate at least a composition datum that includes body data such as a complaint of stomach bloating and cramping and desired dietary state data that includes a gluten free diet. In an embodiment, a user may not have a conclusive label such as if a user has not been diagnosed with any medical condition or if a user previously healed a medical condition or disease state. In an embodiment, a user may generate a dietary response that may not contain a preference for a particular diet or way of eating.

With continued reference to FIG. 13, at least an element of desired dietary state data 120 may be received as a function of a user conclusive label. User conclusive label may include any of the user conclusive labels as described above in reference to FIG. 11. For example, user conclusive label may contain diagnostic information such as a certain physical condition that a user may be dealing with. In such an instance, an element of desired dietary state data 120 may be generated by a functional medicine health professional through graphical user interface 140 for instance. For example and without limitation, user with a conclusive label containing a diagnosis of diabetes may be utilized by a functional medicine physician to generate at least an element of desired dietary state data 120 that includes a recommendation of a low carbohydrate diet so as to minimize insulin spikes that may be experienced by a use with diabetes. In yet another non-limiting example, a conclusive label containing a diagnosis of two copies of the APOE4 gene associated with a significant increased risk for Alzheimer's disease may be utilized by a health professional such as a dietician or nutritionist to generate at least a desired dietary state that includes a vegan diet. Receiving at least an element of desired dietary state data 120 may be received as a function of a user generated response. For instance and without limitation, a user may enter responses to questions about dietary preferences and eating habits through for example graphical user interface 140, which may then generate a desired dietary state for a user. For example, a user may enter information through graphical user interface 140 such as habitually enjoying three meals per day which may be utilized to generate a desired dietary state such as the Mediterranean diet. In yet another non-limiting example, a user may enter a response to a question that describes user's aversion to certain food elements such as animal protein, which may be used to generate a desired dietary state that recommends a vegetarian diet or a vegan diet.

With continued reference to FIG. 13, at least a server 104 is configured to receive at least a user conclusive label containing at least an incompatible food element as a function of at least a conclusive label neutralizer. Conclusive label neutralizer may include any of the conclusive label neutralizers as described above in reference to FIG. 1. For example, a conclusive label neutralizer such as a medication used to treat epilepsy may be utilized to generate at least an incompatible food element that includes grapefruit and grapefruit containing food elements. In yet another non-limiting example, a conclusive label neutralizer containing an antibiotic such as metronidazole may be utilized to generate at least an incompatible food element that includes alcohol and alcohol containing food elements. At least a server 104 is configured to receive at least a user dietary response containing at least an acute vibrancy input, at least a chronic vibrancy input, and at least a longevity vibrancy input. Acute vibrancy input may include any of the acute vibrancy inputs as described above in reference to FIG. 1. For example, acute vibrancy input may include a user's short term dietary response which may include a desire to eliminate simple carbohydrates for three weeks in order to lose weight and fit into a dress for a special event. Chronic vibrancy input may include any of the chronic vibrancy inputs as described above in reference to FIG. 1. Chronic vibrancy input may include a user's chronic dietary response which may include a user's desire to eliminate white sugar from diet or a desire to not consume trans-fats. Longevity vibrancy input may include any of the longevity vibrancy inputs as described above in reference to FIG. 1. Longevity vibrancy input may include a user's lifelong dietary response such as a desire to eliminate all artificial sweeteners from the diet or a desire to consume at least three servings of vegetables each day.

With continued reference to FIG. 13, at step 1310 at least a server 104 selects at least a correlated dataset containing a plurality of data entries wherein each dataset contains at least a datum of body data and at least a correlated compatible food element as a function of the at least a composition datum 108. Datasets may include any of the datasets as described herein. Datasets may be selected from body database 124. Datasets contained within body database 124 may be categorized and/or organized by any of the methodologies as described above in reference to FIG. 1 and FIG. 2. In an embodiment, at least a dataset may be selected by extracting at least a physiological trait from at least a composition datum 108 and matching the at least a physiological trait to at least a correlated dataset containing at least an element of the at least a physiological trait. At least a physiological trait may be extracted from at least a composition datum 108 utilizing parsing module 148 and/or language processing module 144 as described above in more detail in reference to FIG. 1. Physiological trait may include any of the physiological traits as described herein. For example, parsing module 148 and language processing module 144 may extract at least a physiological trait such as a particular nutrition biomarker which may be utilized to match the particular nutrition biomarker to a dataset contained within body database that contains the particular nutrition biomarker. In an embodiment, datasets contained within body database 124 may be organized and categorized according to physiological traits. For example, a physiological trait relating to MTHFR genotype extracted from at least a composition datum 108 may be matched to a dataset contained within body database that is categorized as belonging to a category of physiological traits such as gene nutrition biomarkers. In yet another non-limiting example, a physiological trait relating to a microbiome population of a user's gut may be matched to a dataset contained within body database that is categorized as belonging to a category of physiological traits such as microbiome nutrition biomarkers.

With continued reference to FIG. 13, at step 1315 at least a server creates at least an unsupervised machine-learning algorithm the at least an unsupervised machine-learning algorithm further comprises generating a hierarchical clustering model 160 to output at least a compatible food element as a function of the at least a composition datum 108 and the at least a correlated dataset. Unsupervised machine-learning algorithm may include any of the unsupervised machine-learning algorithms as described herein. Hierarchical clustering model 160 may include any of the hierarchical clustering model 160 as described above in reference to FIGS. 1-13. Hierarchical clustering model 160 may output at least a compatible food element output. Compatible food element output may include any of the compatible food element outputs as described above in reference to FIGS. 1-13. In an embodiment unsupervised machine-learning algorithm may be created by an unsupervised learning module 176. Unsupervised learning module 156 may generate other unsupervised learning models including for example anomaly detection model, data clustering model, and other unsupervised learning models. In an embodiment, datasets utilized to generate unsupervised learning models including hierarchical clustering model 160 may be obtained from body database as described above in more detail in reference to FIG. 4. In an embodiment, a plurality of datasets may be selected from body database and utilized to generate hierarchical clustering model 160 as described above in more detail in reference to FIG. 5. Datasets contained within body database may be obtained from expert input and from health record database. For example, datasets contained within body database may be obtained from medical records that have personal identifying information removed or from the results of patient surveys as described above in more detail in reference to FIG. 6.

With continued reference to FIG. 13, system 100 may create a supervised machine learning model 188 in addition to unsupervised machine learning model. Supervised machine learning model 188 may include any of the supervised machine learning model 188 as described above in reference to FIGS. 1-13. In an embodiment, at least a server 104 and/or supervised learning module 176 may select at least a first training set 184, create at least a supervised machine learning model 188 using the at least a first training set 184 wherein the at least a supervised machine learning model 188 relates body data to compatible food elements and generates at least a compatible food element output as a function of the at least a composition datum 108 and the at least a first training set 184. Training set may include any of the training sets and training data as described above in reference to FIGS. 1-13. In an embodiment, first training set 184 may including selecting the at least a correlated dataset to be utilized as first training set 184. First training set 184 may be selected by categorizing at least a composition datum 108 to contain at least a physiological label and selecting at least a first training set 184 as a function of the at least a physiological label. Physiological label may include any of the physiological labels ad described above in reference to FIGS. 1-13, For example, a physiological label may indicate a particular body dimension that is categorized as containing a particular root cause pillars of disease. In an embodiment, at least a composition datum 108 categorized as relating to gut wall body dimension may be utilized to select at least a first training set 184 that relates gut wall data to compatible food elements. In such an instance, training sets may be organized within training set database 180 according to body dimension for example.

With continued reference to FIG. 13, at step 1320 at least a server generates at least a vibrant compatibility plan 192 wherein the at least a vibrant compatibility plan 192 further comprises a plurality of compatible food elements each containing at least a food element compatibility index value as a function of the at least a hierarchical clustering model 160. Food element compatibility index value may include any of the food element compatibility index values as described above in reference to FIGS. 1-13. In an embodiment, generating at least a vibrant compatibility plan 192 may include retrieving at least a food element compatibility index value correlated to at least a food element from a database and ranking the at least a food element as a function of the at least a food element compatibility index value. Food element compatibility index value may be contained within a food element compatibility index value database 168 as described above in reference to FIG. 7 and FIG. 8. Food element compatibility index value may be calculated as a function of the at least a composition datum 108 and the at least a first food element profile. First food element profile may include any of the first food element profiles as described above in reference to FIGS. 1-13. Food element profiles may be contained within food element profile database 172 as described above in reference to FIG. 9, In an embodiment, food element profile database 172 may contain scores for different components of a food element including for example, a mineral score, a vitamin score, an electrolyte score, an antioxidant score, an amino acid score, and a micronutrient score.

With continued reference to FIG. 13, generating at least a vibrant compatibility plan 192 may include generating a sequencing instruction set wherein the sequencing instruction set contains at least an optimal combination of at least a first compatible food element and at least a second compatible food element as a function of the at least a desired dietary state. In an embodiment, sequencing instruction set may include an optimal combination of food elements as a function of at least a desired dietary state. For example, sequencing instruction set may include an optimal combination of grass fed beef and broccoli for a user with a desired dietary state of a paleo diet while sequencing instruction set may include an optimal combination of millet and eggplant for a user with a desired dietary state of macrobiotic diet. In an embodiment, vibrant compatibility plan may include a ranking of compatible food elements as a function of food element compatibility index value score. For instance and without limitation, vibrant compatibility plan may include a hierarchy of compatible food elements listed in descending order of compatibility whereby food elements containing the highest food element compatibility index score may be listed first.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 14:
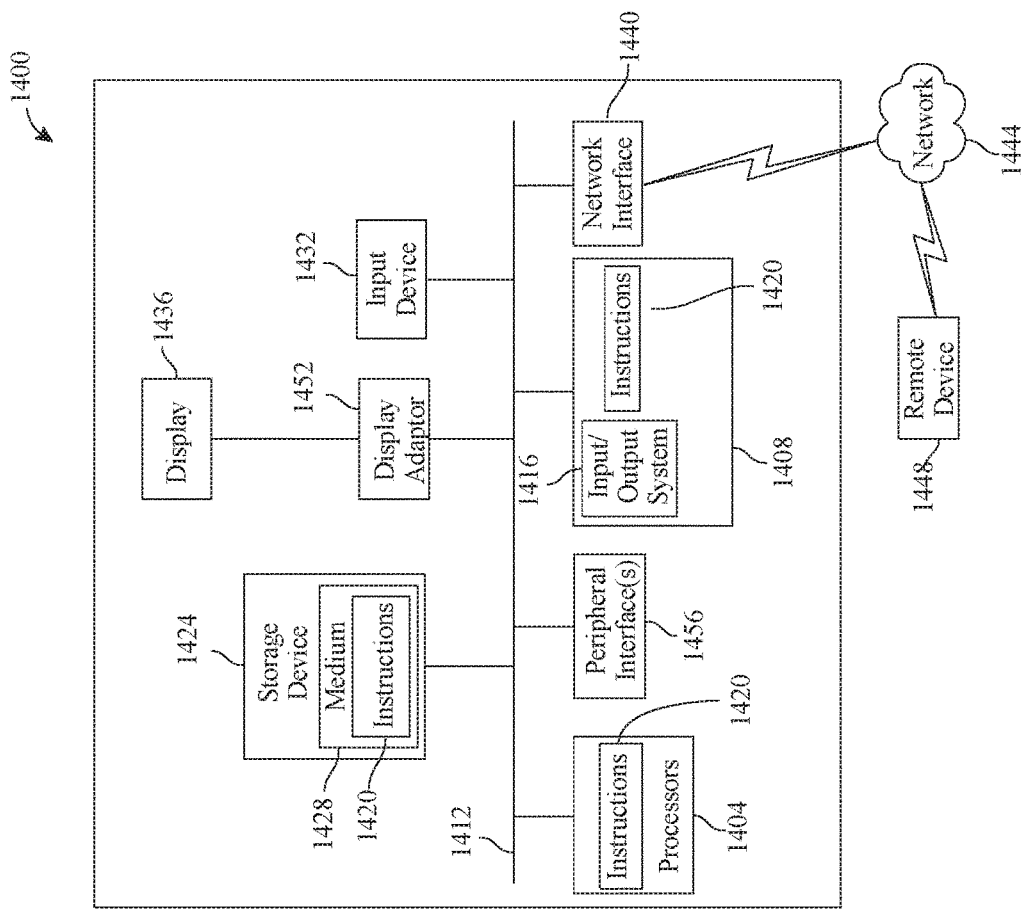
FIG. 14 is a block diagram of a computing system that can be used to implement any one or more of the methodologies disclosed herein and any one or more portions thereof.

FIG. 14 shows a diagrammatic representation of one embodiment of a computing device in the exemplary form of a computer system 1400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1400 includes a processor 1404 and a memory 1408 that communicate with each other, and with other components, via a bus 1412. Bus 1412 may include any of several types of bus structures including, but not limited to, a memory bus, a memory controller, a peripheral bus, a local bus, and any combinations thereof, using any of a variety of bus architectures.

Memory 1408 may include various components (e.g., machine-readable media) including, but not limited to, a random access memory component, a read only component, and any combinations thereof. In one example, a basic input/output system 1416 (BIOS), including basic routines that help to transfer information between elements within computer system 1400, such as during start-up, may be stored in memory 1408. Memory 1408 may also include (e.g., stored on one or more machine-readable media) instructions (e.g., software) 1420 embodying any one or more of the aspects and/or methodologies of the present disclosure. In another example, memory 1408 may further include any number of program modules including, but not limited to, an operating system, one or more application programs, other program modules, program data, and any combinations thereof.

Computer system 1400 may also include a storage device 1424. Examples of a storage device (e.g., storage device 1424) include, but are not limited to, a hard disk drive, a magnetic disk drive, an optical disc drive in combination with an optical medium, a solid-state memory device, and any combinations thereof. Storage device 1424 may be connected to bus 1412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1424 (or one or more components thereof) may be removably interfaced with computer system 1400 (e.g., via an external port connector (not shown)). Particularly, storage device 1424 and an associated machine-readable medium 1428 may provide nonvolatile and/or volatile storage of machine-readable instructions, data structures, program modules, and/or other data for computer system 1400. In one example, software 1420 may reside, completely or partially, within machine-readable medium 1428. In another example, software 1420 may reside, completely or partially, within processor 1404.

Computer system 1400 may also include an input device 1432. In one example, a user of computer system 1400 may enter commands and/or other information into computer system 1400 via input device 1432. Examples of an input device 1432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1432 may be interfaced to bus 1412 via any of a variety of interfaces (not shown) including, but not limited to, a serial interface, a parallel interface, a game port, a USB interface, a FIRE-WIRE interface, a direct interface to bus 1412, and any combinations thereof. Input device 1432 may include a touch screen interface that may be a part of or separate from display 1436, discussed further below. Input device 1432 may be utilized as a user selection device for selecting one or more graphical representations in a graphical interface as described above.

A user may also input commands and/or other information to computer system 1400 via storage device 1424 (e.g., a removable disk drive, a flash drive, etc.) and/or network interface device 1440. A network interface device, such as network interface device 1440, may be utilized for connecting computer system 1400 to one or more of a variety of networks, such as network 1444, and one or more remote devices 1448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1444, may employ a wired and/or a wireless mode of communication. In general, any network topology may be used. Information (e.g., data, software 1420, etc.) may be communicated to and/or from computer system 1400 via network interface device 1440.

Computer system 1400 may further include a video display adapter 1452 for communicating a displayable image to a display device, such as display device 1436. Examples of a display device include, but are not limited to, a liquid crystal display (LCD), a cathode ray tube (CRT), a plasma display, a light emitting diode (LED) display, and any combinations thereof. Display adapter 1452 and display device 1436 may be utilized in combination with processor 1404 to provide graphical representations of aspects of the present disclosure. In addition to a display device, computer system 1400 may include one or more other peripheral output devices including, but not limited to, an audio speaker, a printer, and any combinations thereof. Such peripheral output devices may be connected to bus 1412 via a peripheral interface 1456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a vibrant compatibility plan using artificial intelligence, the system comprising:
   at least a server, the at least a server designed and configured to:
   receive at least a composition datum from a user client device, generated as a function of at least a user conclusive label and at least a user dietary response, wherein the at least a composition datum further comprises at least an element of user body data and at least an element of desired dietary state data and the at least a user conclusive label contains at least an incompatible food element generated as a function of at least a conclusive label neutralizer;
   select at least a correlated dataset containing a plurality of data entries wherein the at least a correlated dataset contains at least a datum of body data and at least a correlated compatible food element as a function of the at least a composition datum;
   extract at least a physiological trait from the at least a composition datum; and
   match the at least a physiological trait to at least a correlated dataset containing at least an element of the at least a physiological trait;
   create at least an unsupervised machine-learning model wherein the at least an unsupervised machine-learning model further comprises generating a hierarchical clustering model to output at least a compatible food element as a function of the at least a composition datum and the at least a correlated dataset;
   generate at least a vibrant compatibility plan wherein the at least a vibrant compatibility plan further comprises a plurality of compatible food elements each containing at least a food element compatibility index value score as a function of the at least a hierarchical clustering model;
   transmit the at least a vibrant compatibility plan to the user client device; and
   display the at least a vibrant compatibility plan through a graphical user interface (GUI) of the user client device.

2. The system of claim 1, wherein the at least a server is further configured to receive at least a user dietary response containing at least an acute vibrancy input, at least a chronic vibrancy input, and at least a longevity vibrancy input.

3. The system of claim 1, wherein the at least a server is further configured to:
   retrieve at least a food element compatibility index value correlated to at least a food element from a database; and
   rank the at least a food element as a function of the at least a food element compatibility index value.

4. The system of claim 3, wherein the at least a food element compatibility index value is calculated as a function of the at least a composition datum and at least a food element profile.

5. The system of claim 1, wherein the at least a server further comprises a supervised module operating on the at least a server wherein the supervised module is designed and configured to:
   receive at least a composition datum;
   select at least a first training set;
   create at least a supervised machine-learning model using the at least a first training set wherein the at least a supervised machine-learning model relates body data to compatible food elements; and
   generate at least a compatible food element output as function of the at least a composition datum and the at least a first training set.

6. The system of claim 5, wherein the at least a first training set further comprises the at least a correlated dataset.

7. The system of claim 5, wherein the at least a supervised module is further configured to:
   categorize the at least an element of user body data to contain at least a physiological label; and select at least a first training set as a function of the at least a physiological label.

8. The system of claim 1, wherein the at least a server is further configured to generate at least a vibrant compatibility plan containing a sequencing instruction set, wherein the sequencing instruction set contains at least an optimal combination of at least a first compatible food element and at least a second compatible food element as a function of the at least an element of desired dietary state data.

9. A method of generating a vibrant compatibility plan using artificial intelligence, the method comprising:
    receiving by at least a server at least a composition datum from a user client device, generated as a function of at least a user conclusive label and at least a user dietary response, wherein the at least a composition datum further comprises at least an element of user body data and at least an element of desired dietary state data and the at least a user conclusive label contains at least an incompatible food element generated as a function of at least a conclusive label neutralizer;
    selecting by the at least a server at least a correlated dataset containing a plurality of data entries wherein the at least a correlated dataset contains at least a datum of body data and at least a correlated compatible food element as a function of the at least a composition datum;
    extracting at least a physiological trait from at least a composition datum;
    matching the at least a physiological trait to at least a correlated dataset containing at least an element of the at least a physiological trait;
    creating by the at least a server at least an unsupervised machine-learning model wherein the at least an unsupervised machine-learning model further comprises generating a hierarchical clustering model to output at least a compatible food element as a function of the at least a composition datum and the at least a correlated dataset; and
    generating by the at least a server at least a vibrant compatibility plan wherein the at least a vibrant compatibility plan further comprises a plurality of compatible food elements each containing a least a food element compatibility index value score as a function of the at least a hierarchical clustering model.

10. The method of claim 9, wherein receiving at least a composition datum further comprises receiving at least a user dietary response containing at least an acute vibrancy input, at least a chronic vibrancy input, and at least a longevity vibrancy input.

11. The method of claim 9, wherein generating at least a vibrant compatibility plan further comprises:
    retrieving at least a food element compatibility index value correlated to at least a food element from a database; and
    ranking the at least a food element as a function of the at least a food element compatibility index value.

12. The method of claim 11, wherein the at least a food element compatibility index value is calculated as a function of the at least a composition datum and at least a first food element profile.

13. The method of claim 9 further comprising:
    receiving at least a composition datum;
    selecting at least a first training set;
    creating at least a supervised machine-learning model using the at least a first training set wherein the at least a supervised machine-learning model relates body data to compatible food elements; and
    generating at least a compatible food element a function of the at least a composition datum and the at least a first training set.

14. The method of claim 13, wherein selecting the at least a first training set further comprises selecting the at least a correlated dataset.

15. The method of claim 13, wherein selecting at least a first training set further comprises:
    categorizing the at least a composition datum to contain at least a physiological label; and
    selecting at least a first training set as a function of the at least a physiological label.

16. The method of claim 9 further comprising generating at least a vibrant compatibility plan containing a sequencing instruction set, wherein the sequencing instruction set contains at least an optimal combination of at least a first compatible food element and at least a second compatible food element as a function of the at least an element of desired dietary state data.

* * * * *